(12) United States Patent
Rich et al.

(10) Patent No.: US 10,557,780 B2
(45) Date of Patent: Feb. 11, 2020

(54) BOARD TESTING APPARATUS

(71) Applicant: DS Smith Packaging Ltd, London (GB)

(72) Inventors: David George Rich, Yorkshire (GB); Lyndon Geraint Jenkins, Monmouthshire (GB)

(73) Assignee: DS SMITH PACKAGING LTD, London (GB)

( * ) Notice: Subject to any disclaimer, the term of this patent is extended or adjusted under 35 U.S.C. 154(b) by 0 days.

(21) Appl. No.: 16/366,775

(22) Filed: Mar. 27, 2019

(65) Prior Publication Data

US 2019/0226955 A1 Jul. 25, 2019

Related U.S. Application Data

(63) Continuation of application No. 15/111,560, filed as application No. PCT/GB2015/050002 on Jan. 2, 2015, now Pat. No. 10,267,716.

(30) Foreign Application Priority Data

Jan. 17, 2014 (GB) .................................. 1400829.6

(51) Int. Cl.
*G01N 3/08* (2006.01)
*G01N 3/20* (2006.01)
*G01N 33/34* (2006.01)

(52) U.S. Cl.
CPC ................. *G01N 3/08* (2013.01); *G01N 3/20* (2013.01); *G01N 33/346* (2013.01)

(58) Field of Classification Search
USPC .................................................. 73/818, 825
See application file for complete search history.

(56) References Cited

U.S. PATENT DOCUMENTS 5,038,603 A * 8/1991 Crittenden ............ G01L 5/0038
73/49.5
5,297,062 A 3/1994 Cresson et al.
(Continued)

FOREIGN PATENT DOCUMENTS

| CN | 1395684 | 2/2003 | |
| CN | 102680319 | 9/2012 | |
| EP | 0491234 A2 * | 6/1992 | ............. G01N 19/02 |

OTHER PUBLICATIONS

Office Action which issued for CN201580004966.5 dated Aug. 27, 2018.
(Continued)

*Primary Examiner* — Clayton E. LaBalle
*Assistant Examiner* — Warren K Fenwick
(74) *Attorney, Agent, or Firm* — Timothy M. McCarthy; Clark Hill PLC

(57) ABSTRACT

A board testing apparatus and method and in particular a testing apparatus for testing a board made of a corrugated material, such as corrugated cardboard, for failure characteristics. The method comprises taking a corrugated board from a corrugator or converter, locating at least a part of the board into a testing machine, performing a non-destructive compression test on a sample region of the part of the board within the machine and providing a compression test characteristic reading of that region of the board, comparing that characteristic reading against a predefined acceptable compression test characteristic reading that design of corrugated board should have and concluding from the comparison as to whether the board, or that sample region of the board, meets a required compression stiffness parameter.

9 Claims, 18 Drawing Sheets

(56) References Cited

U.S. PATENT DOCUMENTS

| | | | | |
|---|---|---|---|---|
| 5,511,432 A * | 4/1996 | Holmes | ................... | G01N 3/20 |
| | | | | 73/856 |
| 6,041,661 A * | 3/2000 | McKinlay | ............ | G01N 33/346 |
| | | | | 73/849 |
| 6,053,052 A * | 4/2000 | Starostovic | .............. | G01N 3/20 |
| | | | | 73/851 |
| 6,386,027 B1 * | 5/2002 | Westin | ..................... | G01N 3/08 |
| | | | | 73/159 |
| 7,194,916 B2 * | 3/2007 | Ouellet | ................... | G01N 3/20 |
| | | | | 73/852 |
| 2003/0136199 A1 * | 7/2003 | Singleton | ............. | G01N 33/346 |
| | | | | 73/846 |
| 2003/0226404 A1 * | 12/2003 | Ouellet | ................... | G01N 3/20 |
| | | | | 73/849 |
| 2008/0276720 A1 * | 11/2008 | Chalmers | ................ | G01N 3/32 |
| | | | | 73/847 |

OTHER PUBLICATIONS

Office Action which issued for CN201580004966.5 dated Jul. 12, 2019.

* cited by examiner

BOARD TESTING APPARATUS

PRIORITY

This application is a continuation of U.S. patent application Ser. No. 15/111,560, filed on Jul. 14, 2016, which was a national stage entry of PCT/GB2015/050002, filed on Jan. 2, 2015, which claimed priority from GB Application No. 1400829.6, filed on Jan. 17, 2014, the disclosures of all of which are incorporated herein.

The present invention relates to a board testing apparatus and method and in particular a testing apparatus for testing a board made of a corrugated material, such as corrugated cardboard, for failure characteristics. Such failure characteristics may have resulted from over processing within the corrugator or a subsequent conversion process, such as a print applying process or a cutting/scoring/folding/assembly process. These processes typically utilise rollers for feeding, transporting or processing the board, and those rollers can cause damage to the board, especially if set up with incorrect or inappropriate pressures or gap widths. The typical damage is an over-flexure of the flute within the board, which can result in a significant degree of weakening of the board as a whole, even when no visual damage is apparent—the over flexed flute can typically bounce back elastically, even though the strength is resultantly compromised, thus masking the damage.

There is also an on-going desire for optimising the weight of materials used in packaging. Having a test procedure to quantify the strength of a particular board would therefore be useful to allow fine tuning of the weight of the materials used in the board while still arriving at the target strength capability, or simply maximising that strength by allowing the processing of the board to be better controlled or managed.

There is also a constant requirement for maintaining a consistent quality for the products, such as blanks or the actual assembled packaging or boxes. There can be in this respect both the visually apparent quality, i.e. a lack of blemishes, plus also the structural characteristic quality, such as the strength of the board. Testing the visual characteristics of packaging is typically able to be done in line using a camera array or a visual inspection. However, checking the structural properties of the product is less easy, and available tests are commonly destructive in nature, or are often needing to be undertaken out of and away from the assembly line, whereupon they can be either impractical or a cause for significant machinery downtime. For example, if a cardboard blank manufacturing line is assembling or creating between 25 and 30 different forms of packaging in a day and if each product test involves a 5 to 10 minute testing process involving removal of a sample product while the assembly line sits in a stand-down mode, removal from that sample product one or more test samples (or assembly of that sample product into a box shape for a box-crush test), taking that sample to a testing machine for testing, carrying out the test, reviewing the results and concluding on whether the product meets the requirements, prior to then making any necessary adjustments to the assembly line (such as roller gaps or pressures), and then subsequent tests to validate the correction achieved by the adjustment, then those 5 to 10 minutes multiplied by 30 product lines, and then multiplied by the number of sequential tests needed to provide the desired correction, is the equivalent of at least three to six hours of downtime per day! It would therefore be desirable to produce a test process which can offer the accuracy of existing processes, but with a reduced amount of downtime.

Regarding the prior art tests, they commonly include box crush or box compression tests (or BCTs). These BCT machines (box compression test machines) test assembled boxes to a point of failure under vertical compression. See, for example, FIG. 1, which schematically shows a typical BCT machine. As shown a box 10 in assembled form is being compressed by an upper plate 12 against a lower plate 14, each plate being mounted on four corner columns 16. The machine as illustrated then further has at least one screw drive 18 for lowering and raising the upper plate 12 relative to the lower plate 14. Force readings are measured by this apparatus (in terms of the resistance to compression versus distance of compression in Newtons (N) and .mu.m) and these readings are fed to a computer 20 such that the readings can then be visualised graphically on a computer screen 22 or compared to accepted norms for such products/materials. The point of failure of the box determines the performance characteristic of the box for the purpose of the customer. This can be seen by the point at which the load force drops off from its peak loading. The box then is either declared a pass or a fail.

This test, however, is a destructive test and is a test that involves the assembly of the box and is also a test that is difficult to perform beside the production line for the blank for the box due to the size of the testing apparatus, and the need for the equipment to be free from interference (such as might be caused by the noise and vibrations of the board/blank production line, and which may cause significant vibration of the assembled box). As a result, tests carried out in this manner tend to be away from the production line and thus too time consuming to be practical for high speed production techniques due to the downtime involved in carrying out the tests on the products.

Bear in mind too that it is also impractical to concurrently continue the production of the products or blanks during the testing process since to do so would produce excessive waste product in the event that the case or box being tested is found to fail its tests, e.g. it being insufficiently structurally strong for meeting the customer's requirements. After all, the production of the cases or boxes occurs with machine feed speeds of perhaps 20 to 400 cases or boxes per minute, each case or box perhaps involving the use or conversion of between 1 and 8 square metres of corrugated material, whereby in the time it takes to do a single box compression test, i.e. in perhaps five minutes, perhaps 2000 cases or more of corrugated material would have been processed and thus wasted in the event of a product failure in the box compression test during a continued production run!

Further, given the profit margins in the production of such boxes, plus the environmental impact of such waste, these levels of wastage are entirely unacceptable both commercially and environmentally, even though the material might ultimately be recyclable. Production runs are thus always stopped during sample testing procedures.

It should also be observed that a different production run cannot be done either, during that down time, since each production run involves different convertor setups, and thus further sample testing.

Recovering this lost down time would thus be of significant benefit to the operators of such machinery.

A particular benefit can be seen where the producer has typical order or production run quantities involving perhaps an average of between 2000 and 5000 cases per order or run, whereby in the time it takes to do the old test, i.e. the five-minutes test, a whole production run would have typically been completed had the test, and thus the long down time, not been necessary. Steps to significantly shorten the down time are therefore very desirable.

In addition to the time disadvantage of the prior art BCT test, the test-to-failure of the cardboard packaging/assembled box is also recognised to be a relatively crude mode of testing since it looks at the ultimate crush strength, rather than the strength of the board per se. Hence a more preferred option of testing would be a test of the material property of the corrugate, rather than the structural property of the box. After all, testing the strength of the corrugate avoids the structural property of the formed blank's corners, for example, providing inaccurate strength test data.

Various techniques have been developed, therefore, to test the quality or strength of the corrugated material itself, and some of these provide a strength characteristic reading for the corrugated material, whereas others look simply at the calliper of the material.

Regarding calliper, a particular form of board will have a known target calliper (i.e. thickness) given its design (i.e. the materials used for the front and back layers, and the flute, and the form of that flute, e.g. be it an A-flute, a B-flute, a C-flute, an E-flute, an F-flute, a G-flute, an N-flute or an R-Flute®). If the thickness, i.e. calliper, of the board post processing, for example as it exits the corrugator that forms it, or at the feed point for the converter apparatus (i.e. prior to the pinch of the feed roller thereof), the convertor apparatus being a machine which might apply print, creases, folds, perforations or other post forming steps, or after it exits that convertor apparatus, is below that target calliper, then it is known to be overly compressed, and thus potentially damaged. This basic test, however, is relatively crude or insensitive to minor crush damage since the corrugation has a tendency to be resilient, and thus it will spring back from a certain degree of compression either fully to the target calliper, or substantially back to that target calliper, thus leaving little indication of the degree of damage caused to the board by that over-compression or minor crush damage.

Another more reliable test is instead a more recently developed test that is known as the dynamic stiffness test or DST. This test measures the resistance characteristics of a sample cut from a corrugated sheet following a twist force applied thereto. See FIG. 2 for a picture of a rig used for such a test. In that figure, a sample 24 is mounted at its ends in two clamps 26, 28, one of which is mounted to a sensor unit 30 and the other of which 28 is fixed to an assembly frame 32. The fixed clamp 28 can be opened and closed using a lever 34. Likewise, the movable clamp 26 can be opened and closed using a lever 36, this time instead at the head 38 of the sensor unit 30. To perform the test, the head 38 is initially rotated relative to the fixed clamp 28 so as to rotate the rotating clamp 26 and thus twist the sample 24. Then, the head 38 is allowed to revert back to its original position, which occurs through an oscillation of the head 38 that is governed by the torsional stiffness and resilience of the sample 24. A reading of the stiffness and resilience of the sample 24 can thus be produced by the sensor unit 30 based for example on the frequency, amplitude and decay rate of that oscillation. That reading thus provides a representative stiffness characteristic figure which provides an indication of any permanent damage that had already occurred to the board, such as damage to the corrugations within the sample 24.

If the corrugations have been damaged, then the stiffness will be lower than if the corrugations are still in an undamaged condition, and the above test provides a clear differentiation between damaged and undamaged samples. This dynamic stiffness test has thus been found to be highly effective in providing quality assurance information about corrugated materials coming out of either a corrugator or a conversion machine (such as a printing machine, a cutting machine or a creasing/perforating machine), and has been used by multiple corrugation manufacturing plants to date. However, the test is relatively slow, and it can have a significant reliance for its accuracy on the diligence of the operator, as will be discussed below:

As shown in FIG. 3, the process of producing the samples 24 involves a manual use of a guide form 40 having two parallel cut guides 42 through which a craft knife such as a Stanley® knife can be used to cut out the sample. Then, to give a consistent length, the guide form 40 is rotated so as to use the outer long edges thereof as a guide for cutting a predetermined length for the samples 24. Those samples can then be mounted within the two clamps 26, 28 and then tested. The sharpness of the blade used can determine whether the samples are cleanly cut, and since a non-clean cut can itself introduce damage to the corrugations/flutes, this makes the use of care, and particularly the use of a sharp knife, important. Likewise the pressure applied onto the guide form 40 can vary from user to user, and if too hard a pressure is applied that too can damage the flutes. Yet further, the gripping of the sample in the clamps can introduce errors or damage, e.g. if clamped too tightly (and not all samples will have a common thickness, e.g. samples from different card types). Finally, although the actual test is quick—approximately 15 seconds, the preparation of the sample out of a sheet removed from the production line, and the mounting of the sample in the testing rig, can make the whole procedure take perhaps 2 or 3 minutes per sample, even for a practiced operator. Thus, although this may be faster than a box compression test, and more accurate than just a calliper test, even this test is too slow to be rolled out to all commercial applications, or for all product runs on a given production line, or for fine tuning a production run through multiple repeat tests following roller calibration adjustments. It is therefore in practice inconsistently, or only irregularly, performed.

It would therefore be desirable to provide a faster, yet similarly accurate, test procedure for use within or beside the production line so as to allow it to be used regularly and consistently and thus to enable a manufacturer to be able to always perform the test and thus better calibrate the roller pressures, and also concurrently to offer to customers a certificate of conformity for the product leaving the production line. This can then provide an assurance to the customer as to the quality, consistency and performance characteristics of the blanks or packaging products provided to them.

According to a first aspect of the present invention there is provided a method of testing a structural characteristic of a corrugated board comprising taking a corrugated board from a corrugator or converter, locating at least a part of the board into a testing machine, performing a non-destructive compression test on a sample region of the part of the board within the machine and providing a compression test characteristic reading of that region of the board, comparing that characteristic reading against a predefined acceptable compression test characteristic reading that that design of corrugated board should have and concluding from the comparison as to whether the board, or that sample region of the board, meets a required compression stiffness parameter.

Preferably the board is a completed blank for forming a box or packaging. Preferably it is tested while still unfolded, or still unassembled into the box. It is possible, however, for the board to be a folded blank, a part folded product or a fully assembled box, albeit preferably with an accessible board edge for insertion into the testing machine. The testing machine preferably has a slot for receiving that edge.

Typically the test is performed on a box, or on a folded blank, or on a part folded product, rather than a flat or unfolded blank, when the board exits the production line in that folded, assembled, or part assembled condition.

An alternative embodiment is where the board to be tested is a sheet of corrugated board prior to passage through a convertor.

Another embodiment is where the same board, blank or folded blank is tested more than once, including a test prior to passage through a convertor and a subsequent test after passage through the convertor. This is a preferred arrangement for initial setup of a production run.

The board is preferred not to be a sample cut from the sheet that exits the production line, but is instead a large corrugated member, such as a completed blank, e.g. having a linear dimension, such as a width or length, of at least 30 cm.

By being straight off the production line, rather than being a sample cut from the sheet that exits the production line, less processing, or even no processing, is needed prior to carrying out the test on the board or sheet. This thus speeds up the test process significantly, potentially allowing multiple tests per minute.

A preferred arrangement is where the test can be carried out on a sheet or board sitting on the feed area of the convertor within 10 seconds, such that taking up the sheet, performing the test and returning the sheet to the feed area takes no more than 10 seconds.

In preferred examples, the sheet or board is preferred to be at least 30 cm wide. More preferably it is also at least 20 cm long. More preferably it is at least 1 m wide and more preferably it is at least 30 cm long.

Previously, completed blanks (or sheets/boards having a dimension larger than 20 cm, 30 cm or 1 m) were generally not able directly to be used in quality test procedures or quality test apparatus since they were too large for the test equipment. Even in a box compression the blanks are not "directly" used—they first need to be folded up to form the box, and thus the box compression test equipment only tested assembled boxes made from the blanks, rather than the blanks themselves.

According to a second aspect of the present invention there is also provided a testing machine adapted to carry out a method of non-destructively testing a structural characteristic of a corrugated board comprising, performing a non-destructive compression test on a sample region of a corrugated board, the board having been taken from a corrugator or converter apparatus and then having been located at least partially into the testing machine, and from that test providing a reading of that sample region's compression test characteristic, comparing that characteristic against a predefined acceptable characteristic that that design of corrugated board should have and concluding as to whether the board, or that region of the board, meets a required compression stiffness parameter, wherein the testing machine comprises:
   a) a support surface on which the region of the board can lay,
   b) a pressure plate with which a testing force can be applied to an opposing side of the board so as to apply a compression force across the thickness of the board towards the support surface,
   c) one or more sensors for sensing a deflection by and a force from the board and
   d) a look-up table for checking sensed data against a predetermined force per deflection parameter.

The method may be as previously described with respect to the first aspect of the invention.

Preferably the compression test involves the provision of a testing apparatus having a slot therein adapted to accommodate the thickness of the board so as to allow the board, or the section thereof to be tested, to be slotted therein.

Preferably the test involves multiple tests of the board, e.g. at different sample regions thereof, so as to provide a range of compression test characteristics across the surface area or width or length of the board. The overall determined characteristic of the board might then be an average of those readings. Multiple test results are not essential, but are preferred, especially for blanks used to form multi-sided objects, since the rollers used in the forming or conversion of the board can be non-uniformly arranged across the width of the sheet passing through those machines, and each side of the to-be-formed object may want to be tested.

Regarding the rollers, inconsistent roller pressures may occur due to incorrect set-up or due to wear on a roller, which may manifest itself as a tapering of a roller, so as to give a non-uniform pressure to the sheet or blank across the width thereof. A barrel taper can also form, and that can result in a wider (or narrower) middle section on the board compared to one or both edge section or sections of the board. Other forms of wear, or incorrect set-up, can even produce undulations across the width or length of the board. Testing at multiple positions can identify localised faults, or incorrect roller alignments, in the production line, thus allowing them to be corrected where possible, often simply through the pressing of a button or buttons on a control panel for the production apparatus.

Since the tests are carried out on a complete blank, rather than samples cut from the blank, the testing can be very rapid. Indeed, with the testing equipment shown in the preferred embodiment, multiple tests, and apparatus adjustments, can be carried out within a minute, whereby a test can be carried out on a first sample, and if a fail is identified, the corrugator or conversion apparatus can be adjusted by changing the press weights or feed speeds or the like (typically via a controller that is button operated, or the above-mentioned control panel) and then a next sample can be run out of the production line and repeat tests carried out on that to see if the problem has been corrected. In this manner it has been found that at least four such checks, and where needed any small pressure/feed alignment changes, can be carried out within a minute whereby the present invention can provide rapid production line set-up times between job orders, or rapid fault identifications and corrections, for the production line. This invention thus can significantly reduce downtime in the production line equipment. This is particularly helpful with board conversion equipment since such machinery may carry out a number of different processes, many of which can have a damaging effect on a sheet of corrugate if carried out incorrectly, or with the incorrect roller setup, such as in respect of gap distances and pressures. These processes can include the application of glue, the application of colours or inks, the addition of barcodes, the addition of folds, creases, score lines, perforations and cuts, plus also the actual assembly of the product itself in some situations. These convertors also have feed rollers for pinching the blank for feeding it into the machine, and that can easily damage a blank if incorrectly set up.

With the present invention, the board, i.e. the material of the corrugate, can be tested either in a flat form or an assembled (or part assembled) form so long as, in the preferred embodiment, an edge of the board can be accessed and inserted into the slot of the testing apparatus.

It is preferred that the test is carried out on more than one area of the blank and the results be compared or subjected to an averaging process, such that either localised faults can be identified, and thus trends can be noted, or so that only a minor flaw, or a freak-flaw, would not necessarily cause the board as a whole to be a fail. This avoids localised or occasional/erratic flaws from causing significant product wastage. This is beneficial since generally speaking the integrity of a whole box is not compromised by just a single, localised, area of weakness.

Since no test samples need to be cut from the board, the present invention also avoids health and safety issues arising from the presence of knifes or cutting equipment adjacent to but separate from the production line on the factory floor. This is a further advantage of the present invention.

According to a third aspect of the present invention there is also provided a novel mode of testing which focuses on the failure characteristics of a corrugate, rather than the point of absolute failure:

It has been recognised by the present inventors that a non-damaged corrugate does not have a singular point of failure, but is instead characterised by a multi-stage mode of failure having three distinct failure points. This is clear from a review of the deflection versus load traces within FIGS. 5 to 10. The present inventors have therefore made use of this specific failure characteristic to fine tune a test apparatus so as to provide more rapid test results, and in a non-destructive manner. Like with the dynamic stiffness test, but unlike the box compression test, a complete failure of the board is not a part of the test, whereby the test of the present invention can be carried out quickly on a sample once that sample is located within the testing apparatus. However, unlike the dynamic stiffness test, the present invention can be carried out on the board itself, rather than requiring a sample to be cut therefrom. According to the third aspect of the present invention, therefore, there is provided a board testing procedure carried out by a testing machine, the method comprising placing a board of a known type of corrugated material between a support plate and a pressure plate of the machine, loading the board by movement of the pressure plate relative to the support plate so as to compress the board therebetween, taking load and deflection readings with one or more sensor mounted on or within the machine, and outputting at least one pair of a load and a deflection reading for comparison with a predetermined reading for that given deflection for that board type, that deflection being a distance not exceeding 90% of a predetermined mean first failure point for that type of corrugated material.

Preferably the method also involves taking a calliper of the board at a point of loading not exceeding 20 N/cm2 at the area of loading, or more preferably 10 N/cm2 at the area of loading, but preferably exceeding 1 N/cm2, or more preferably 3 N/cm2. This calliper can be taken to be a reference calliper at an assumed substantially zero deflection. Such a calliper reading is taken using what's generally referred to as a "soft landing", which typically have the levels of load signified above. This may be five N to 30 N in total in some embodiments. About 10 N is a preferred soft landing loading.

For a typical testing machine, the pressure plate has a flat, disc-like, board-facing surface. Preferably it has a diameter of about 20 mm. As such it has a surface area for bearing against the board of about 3.14 cm2. The shape or diameter may vary, but preferably it has an area between two and 10 cm2.

Preferably the pressure plate is connected to a drive mechanism for imparting a loading force against the blank of up to at least 500 N or in another embodiment of up to at least 1000 N. Preferably the reference calliper, corresponding to an assumed substantially zero deflection, is taken at a loading of between 10 and 40 N.

The method may also comprise taking a zero calliper datum by movement of the pressure plate against the support plate, and then retracting it, all prior to insertion of the board therebetween.

The first failure point for a corrugated board is the deflection point for a board whereat a first peak loading occurs. This corresponds with the point at which a first arch of a flute of the board, i.e. a corrugation, first fails, i.e. it buckles. There is then subsequently a second point failure—which is where the opposing flute arch fails, i.e. it also buckles. There is then a final point failure whereat the flute walls (joining the flute arches) also fail, i.e. they also buckle. This is then considered to be a complete structural failure of the corrugation. FIGS. 35 to 38 provide representative images of the form of these failures for a first type of glued corrugation (wherein the arches are bonded to the top and bottom faces of the board, respectively).

It is preferred that the testing apparatus also takes a calliper measurement for the board since this provides the zero deflection point reference. However, this can also be for cross-referencing within a look-up table that comprises that predetermined reading. The calliper measurement can provide a crude indicator of a failure in the event that the board calliper measurement does not either match or if it varies by more than a predetermined delta from, a predetermined mean calliper measurement for that board type.

It is also preferred that two calliper readings are taken—a first prior to conversion of the board by the convertor apparatus, and then a second after that conversion. This can offer a further crude calliper determination of failure—e.g. if the two calliper readings differ by more than a predetermined amount for the board type, but more usefully it provides additional data for the damage determination.

In a preferred embodiment, the test is looking for a deflection delta for a given loading. In the preferred arrangement this is calculated as the initial calliper measurement (e.g. the feed end calliper (i.e. prior to the convertor pinching it with its feed rollers), minus the panel calliper measurement (i.e. the second calliper measurement—taken after the conversion) plus the deflection measured from that second calliper measurement when that panel is put under the test's pre-set load. That present load may be in the order of 50 to 95% of the sample's board type's predetermined loading for achieving a first failure point, and most preferably at about 85% of that first failure point's loading. If the deflection delta exceeds a target delta, then it is a fail. If not it is a pass.

The use of two callipers (one before and one after conversion) prevent a small post-conversion deflection at that say 85% loading from giving a false positive. After all, if the board was crushed too much by the convertor, it would potentially not elastically recover, and thus would have a smaller calliper at the soft landing point, and it would then have a greater stiffness thereafter (thus deflecting less and causing a false positive, other than for the presence of the pre-conversion calliper correcting for that).

FIGS. 5 to 10 show various traces for various different board types, with various different materials used in the construction thereof, including traces (in some instances)

both for a first test on a board to a certain point of failure, e.g. first or second point, but not third point (complete) failure, and then a follow up test on that same board sample to then show how that partially failed board features a different response to the loading to the point of third point (complete) failure, thus illustrating that it is possible to identify a compressive failure of a board even where a complete failure has not occurred—it can be identified by the lower trace path through at least the point at which first point failure would have been expected.

The present invention is therefore characterised by analysing the force versus deflection data of a board being tested against the expected response for such a board—predetermined through prior testing of a board of the same type that is known to be in good condition.

The invention preferably looks at the loading required to provide a first deflection of the board, that deflection being at a point lying at about 85% of the first failure deflection point, or conversely the deflection achieved following an 85% loading (of the load required to achieve the first failure deflection point) and providing a pass or quality characteristic indication for the board being tested based upon a comparison of the actual force/deflection versus the expected force/deflection for that deflection/force.

Since the first failure point is not crossed, this is a non-destructive test.

Preferably the test deflection or force is between 50 and 90% of the expected deflection or force needed to achieve a first failure point.

Preferably the system comprises a database or lookup table comprising test data for boards of various different types so that the apparatus can look up the appropriate readings for a given board structure. Preferably this look up table has data on the deflection and/or force responses in addition to data on the form of the board itself, such as at least some of the following: flute profile type, material weights and material types, including separate data for at least some of a) top web materials, b) bottom web materials, c) flute materials, d) ply structure (i.e. tri-wall or two wall designs), and e) callipers, plus possibly also not just first point failure deflections/forces, but also second point failure deflections/forces and third point failure deflections/forces.

Preferably for each board structure an identifying "board type code" is assigned whereby the look up table can look up all details for a given board type quickly by referencing that code.

Preferably the test procedure includes a reference test prior to the test on the final board, where that final board is exiting a convertor machine. That reference test can be on a board taken from the corrugator, i.e. prior to passage to the convertor. Another possibility is to take it from the convertor, but prior to it being initially pinched by the feed roller thereon. This is commonly referred to as a feed board.

The reference test allows any damage applied to the board by the corrugator or the converter unit to be separately noted, whereby the corrugator can be adjusted if needed, or instead the converter unit can be adjusted if the damage only occurs in the convertor unit. For example, the convertor unit may need to have its feed roller pressures, its inking roller pressures or its cutting/scoring/perforating/folding roller pressures adjusted to ensure non-damage to the board as it passes therethrough, rather than requiring a trial and error process with the corrugator and the convertor unit for identifying where the damage occurred. It can also provide a correction or reference calliper for badly damaged final board so as to not have the deflection thereof in the post conversion compression test give a false pass.

With the present invention, a test result may be provided within up to 5 seconds or up to 10 seconds of insertion of a board into the testing apparatus, since the degree of compression required to get a reading is small—typically less than 1 mm, and perhaps less than 0.8 mm, or even 0.5 mm, and more preferably up to about 0.4 mm. Different board types can require different degrees of compression for the test to be performed, however, with some requiring only up to a 0.35 mm compression to determine a fail or pass. Since the test can thus be done quickly, multiple tests and adjustments can be made to the converter unit or corrugator within a minute, thus allowing rapid fine tuning of the converter unit or corrugator, thus reducing downtime thereof during order swap-overs, or when there are roller or material supply changes during any given day.

A preferred test apparatus has a feed speed for the loading arm, i.e. the pressure plate, of about 12.5 mm per minute, or between 5 and 20 mm per minute.

The loading used in the test is sometimes referred to as a torque loading. This is due to the form of the drive for the pressure plate—it has a motor and it is the torque output of the motor. For example, therefore, the torque of the motor needed to achieve the first point failure would be the first point failure torque or 100% torque. This is predetermined by testing on sample boards. The torque for the pass/failure test, however, would then be at a percentage of that 100% torque, i.e. between 50 or 95% of that 100% torque, i.e. preferably about 85% of that first failure point torque load. The loading, however, is typically a compression loading of the board, rather than an applied torque on the board itself. Indeed, it is preferred that the loading is not a torque loading on the board or panel, and it instead be more simply just a compression test between the support plate and the pressure plate.

In preferred arrangements, therefore, there may be two options for getting a pass/fail result:
1. input a torque value of circa 85% of first point failure and measure the deflection—if it is less than a target deflection value, then the board is a pass, but if it is more than a target deflection value it is a fail.
2. input a target deflection value for the cylinder to achieve from soft land point and measure the resultant torque required by the cylinder to achieve that target deflection value, and if it is for example about 80% of first point failure torque then the board is good, but if it is much lower, say 30 to 40%, then the board has previously been crushed through first point failure and is thus a fail.

Bear in mind there can be a delta between the pass and fail points—i.e. an "amber" condition, potentially for signifying an inconclusive result, or for building in a margin for accommodating small localised imperfections. This, however, is not essential.

The present invention also provides a pre-formed blank ready for assembly into a packaging or box comprising a top ply, a bottom ply and at least one corrugate therebetween, and additionally comprising a certification with respect to the structural characteristics thereof which has been authenticated during the production run for that blank using the method or apparatus described above or herein.

Preferably the board is a result of an adjusted production run, wherein feedback from the test procedure allowed that adjustment via an adjustment of the corrugator or convertor unit, such as an adjustment of a roller gap, a roller alignment or a roller pressure.

The present invention also provides an apparatus for testing boards of corrugate, the testing apparatus providing a support plate, a pressure plate, a frame, a mechanism for moving the pressure plate relative to the support plate, and sensor equipment, preferably in the form of load sensors and movement sensors for measuring movements and forces experienced by the pressure plate or the support plate or both, and a slot for receiving a board between the support plate and the pressure plate, the slot extending the full width of the apparatus.

Preferably the pressure plate 48 is adapted for movement through a force sensing displacement mechanism 56, thus integrating the load sensor therein along with the displacement sensor.

Preferably the apparatus comprises an integrated screen.

Preferably the screen is a touch screen for controlling the operations of the apparatus.

Preferably the screen indicates pass or fail information of the board. This may be via a traffic light indicator, for example with green or amber for a pass or preliminary pass and red for a fail.

Preferably the apparatus is arranged to take multiple test readings and to provide a pass or fail score based upon multiple readings. This is preferably instead of using just one reading, although individual pass or fail scores for each test can also be provided.

Preferably the multiple results are averaged for providing the pass or fail score.

The movement of the pressure plate might be provided mechanically, hydraulically, pneumatically, through a screw drive or through a belt drive. The preferred means uses a moving coil actuator, due to its accuracy. It may be a voice coil type actuator. Preferably the pressure plate is smaller than the support plate.

Preferably the pressure plate has an outer dimension of not exceeding 30 mm and more preferably is a 25 mm or 20 mm round disc. By providing a small pressure plate, smaller loads are necessary to undertake the testing, since over a larger area, a larger force is needed to provide the total compression necessary to cause deflection of the board.

The apparatus is preferably adapted to undertake any one or more of the testing methods discussed above.

The present invention also provides a corrugated blank manufacturing line characterised by implementation thereon an apparatus as defined above.

The present invention also provides a corrugated blank manufacturing line characterised by implementation on a manufactured blank or product therefrom a method as defined above.

The present invention also provides a corrugated blank manufacturing line characterised by implementation thereon a testing machine as defined above.

The present invention also provides a corrugated blank manufacturing line as defined above having calibrated roller pressures for either its corrugator or its converter for its particular run of blanks or products made from those blanks. Such calibrated rollers produce a more reliably fault free supply of products, thus reducing the likelihood of returns.

The present invention also provides a corrugated blank or product from a run of blanks manufactured on a corrugated blank manufacturing line as defined above, having calibrated roller pressures for either or both its corrugator or its converter for that particular run of blanks or products. The blank can be optimised for material weights due to the use of the inventive corrugated blank manufacturing line, and it will generally be fault free since no over or under pressures were applied thereon by the rollers of its corrugator or its converter.

The present invention also provides a stack or bale of blanks from a run of blanks manufactured on a corrugated blank manufacturing line as defined above having calibrated roller pressures for either or both its corrugator or its converter for that particular run of blanks. The stack or bale can be optimised for material weights due to the use of the inventive corrugated blank manufacturing line, and it will generally be fault free since no over or under pressures were applied to the blanks thereof by the rollers of its corrugator or its converter.

These and other features of the present invention will now be described in further detail with reference to the accompanying drawings in which.

Figure 4:
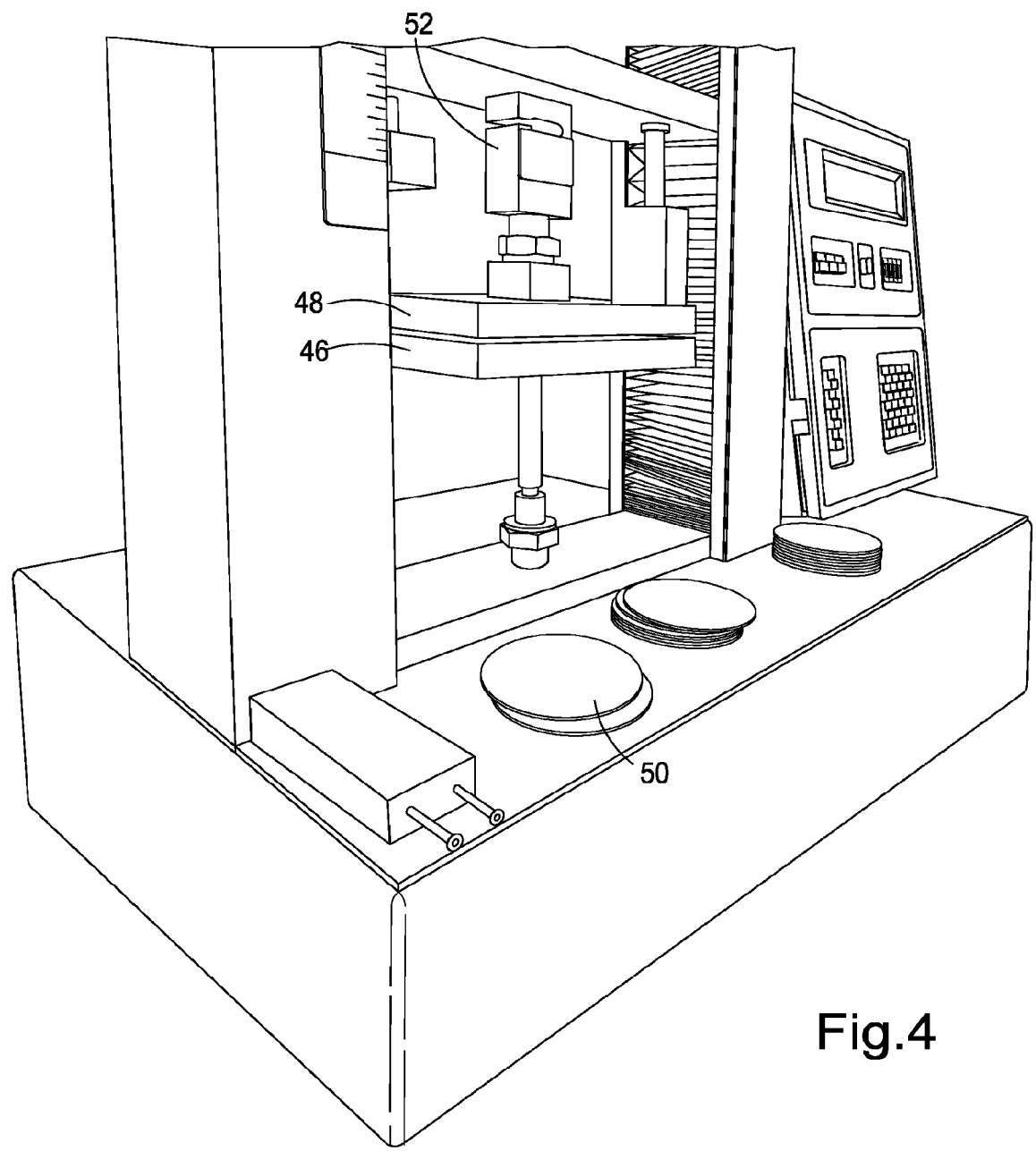
FIG. 4 shows a compression/deflection testing apparatus used for forming data for look-up tables for use in the present invention by testing undamaged samples 50.
Figure 11:
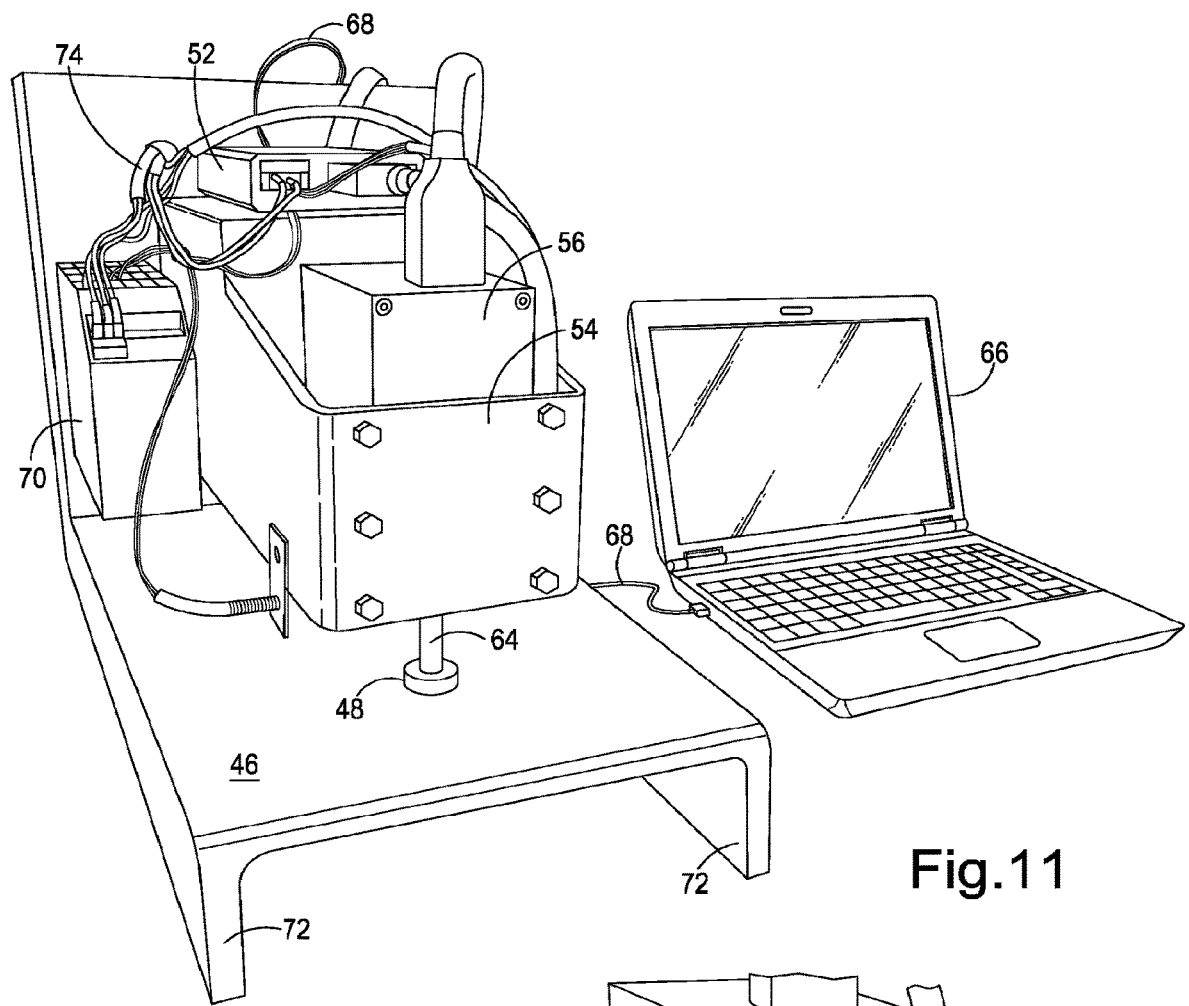
Figure 12:
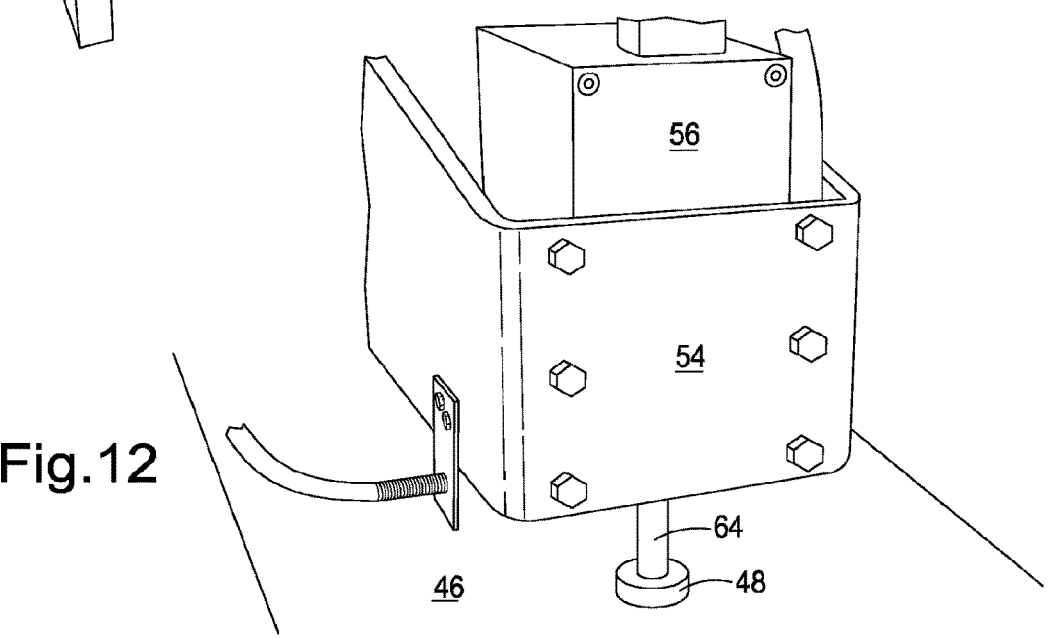
Figure 13:
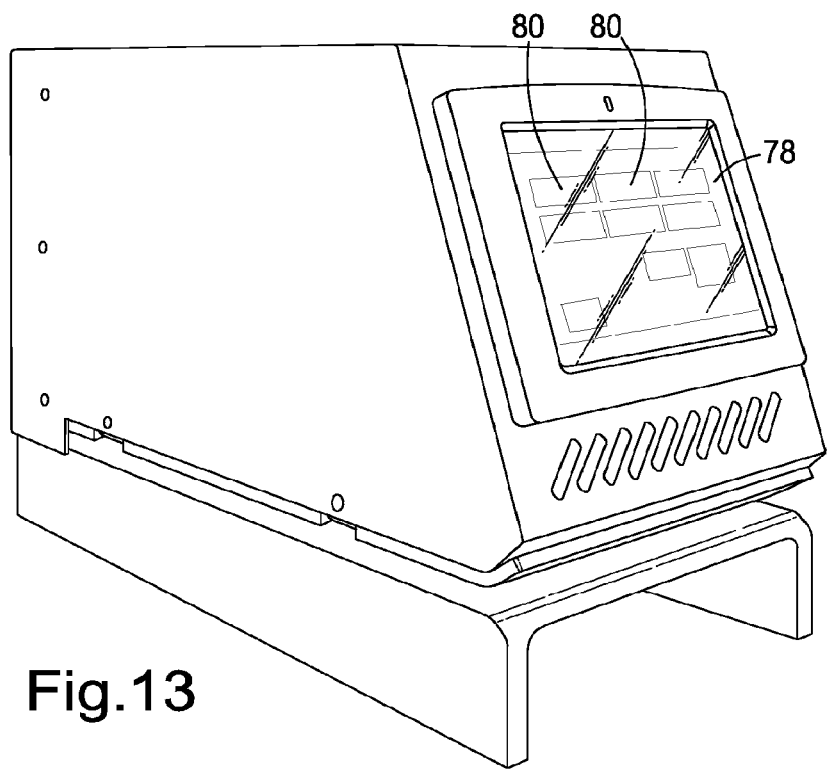
Figure 14:
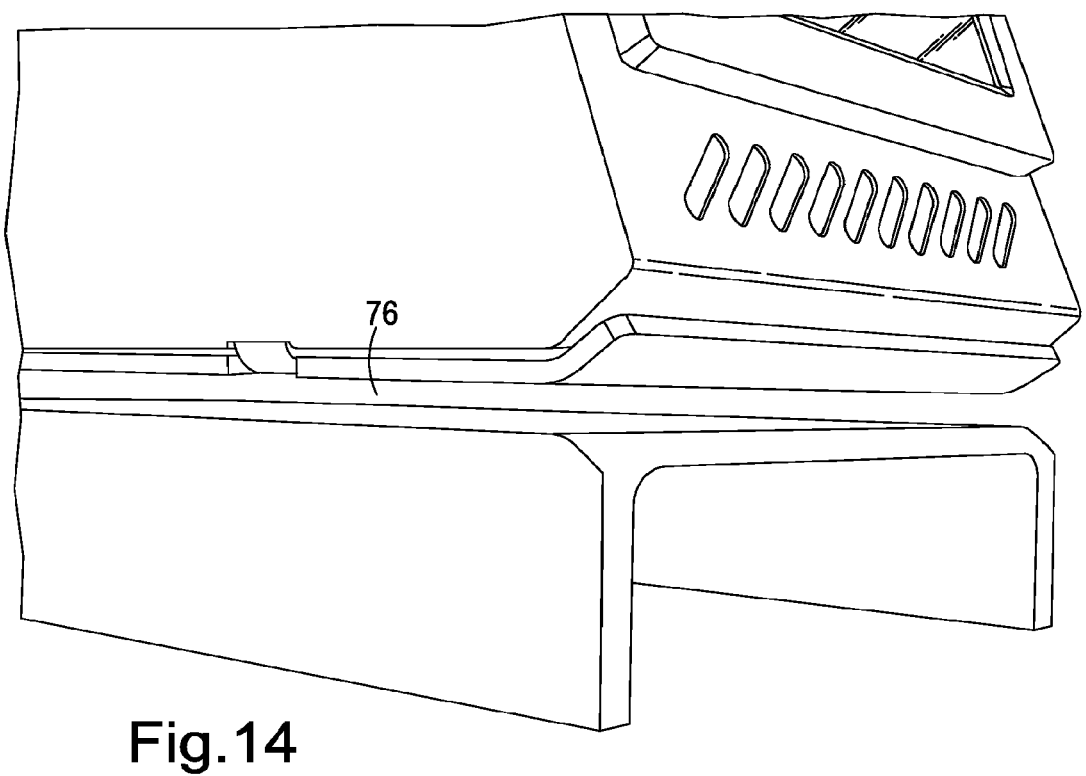
Figure 35:
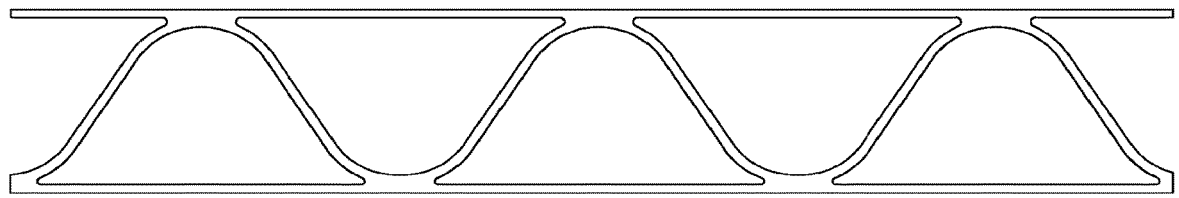
Figure 36:
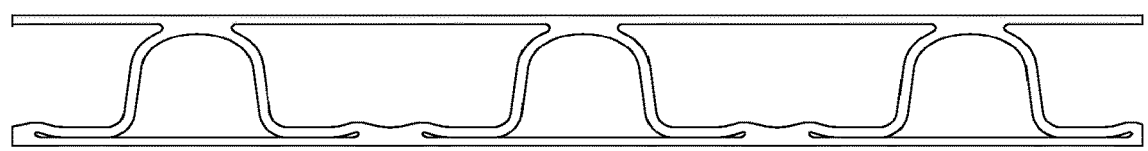
Figure 37:
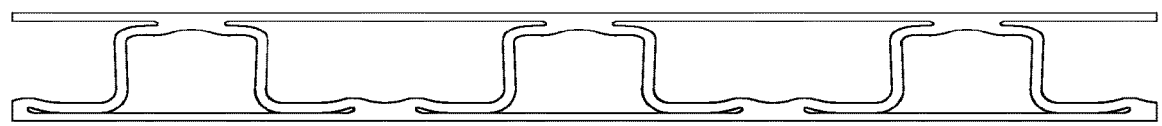
Figure 38:
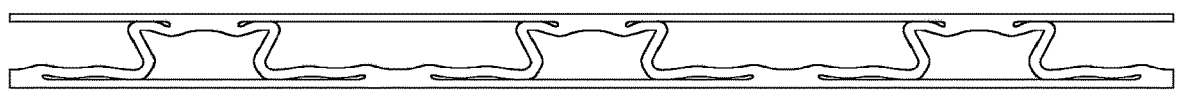

FIGS. 5 to 10 shown test data results or plots from tests carried out using the apparatus of FIG. 4;

FIG. 11 shows a first arrangement for the present invention's board testing apparatus;

FIG. 12 shows a detail of the support plate and pressure plate of that apparatus;

FIGS. 13 and 14 show a further embodiment of a testing apparatus according to the present invention with a slot for receiving a board therein to be tested;

FIGS. 15 to 19 show sample screen layouts for use on the screen of the test apparatus during a preferred testing process;

FIGS. 20 to 34 show a preferred arrangement of testing apparatus and its mode of manufacture;

FIG. 35 schematically illustrates a section through a corrugated sheet having a good corrugation in the core thereof, with the shape of the flutes clearly illustrated;

FIG. 36 shows that same corrugated sheet but after a first point failure wherein the crowns of part of the waveform of the corrugations have collapsed. The height of the board is correspondingly reduced compared to FIG. 35;

FIG. 37 shows that same corrugated sheet after a second point failure wherein the opposite crowns, or all crowns, have now failed. The height of the board is again correspondingly reduced, now compared to FIG. 36; and FIG. 38 shows a complete failure of the corrugation/flutes, whereby both the crowns and the walls between the crowns have failed. This sheet is thus such that the corrugated board has fully collapsed, whereafter the corrugations will provide minimal compression resistance. The height of the board is thus even further reduced, now compared to FIG. 37.

Figure 1:
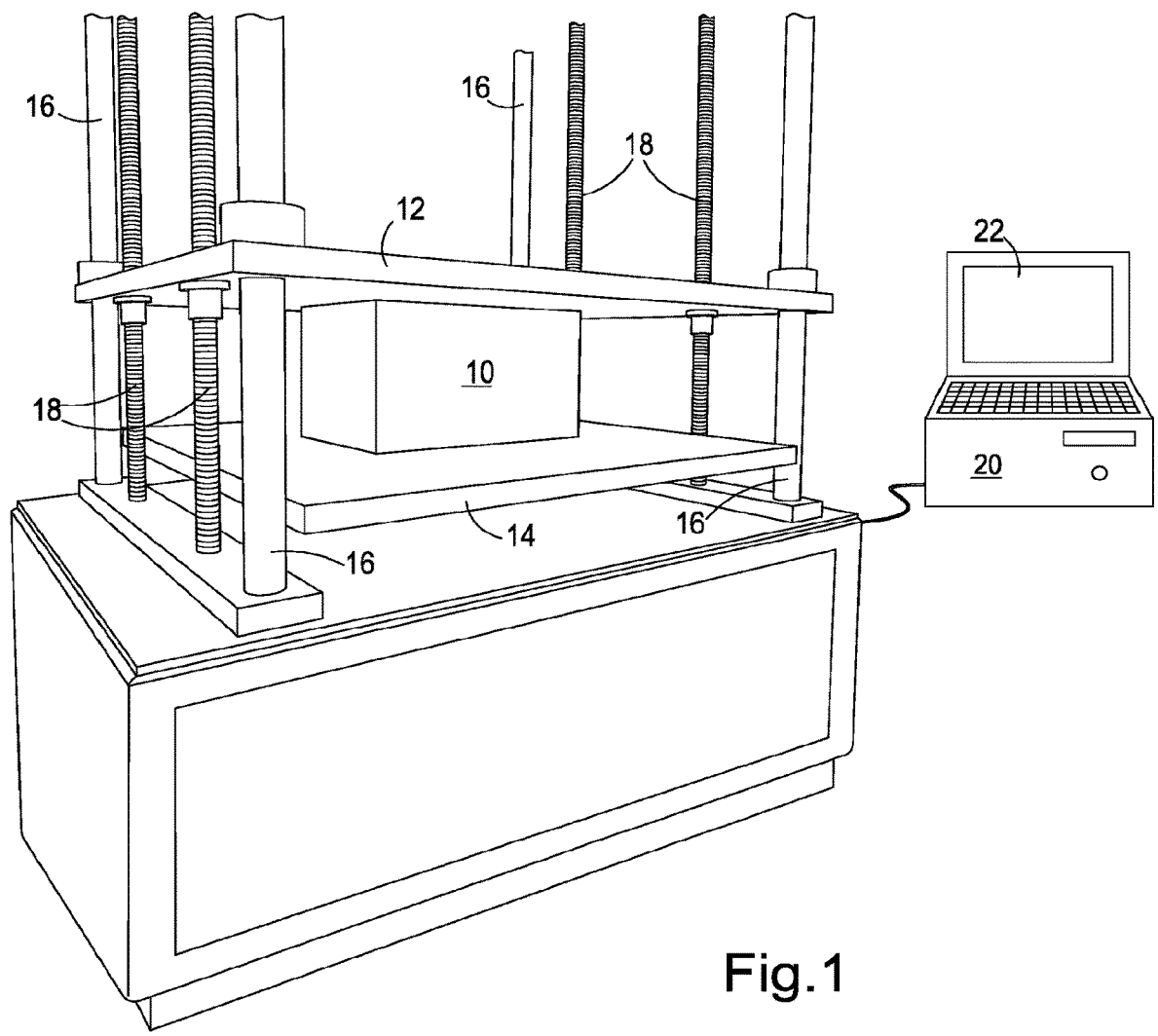
FIG. 1 shows a box testing apparatus.

Referring first of all to FIG. 1, a box compression test (BCT) apparatus is illustrated. As previously discussed, in this apparatus, a box 10 is located between an upper plate 12 and a lower plate 14 and is compressed to the point of failure. Typically the failure is observable as the corners of the box 10, or at the edges running between the upper plate 12 and the lower plate 14—by sight of a propagating crease. This failure also provides a clear drop in the compression support force provided by the box 10, which can readily be seen in a deflection versus force graph, a plot of which may be displayed on an adjacent computer screen 22 of a computer 20. This test is a well-recognised test in the art for providing an absolute compression strength of a box. Unfortunately, however, it is somewhat inaccurate in terms of identifying part failed boards, since the failure identified by the test is determined by the structural failure of the box, rather than the structural failure of the material of the box. It is also relatively slow to perform due to the need to assemble the box prior to undertaking the test and due to the larger deflections needed to achieve the detection of the failure, and thus to provide a "box strength" reading (be that a value or a pass/fail indication—e.g. if there is a target strength).

It is also to be observed that since the whole box is tested, rather than just an area of the box, imperfections in the squareness of the corners, or of the true-ness of the folds, can also lead to significant initial deflections as the box settles into the machine's compression cycle, whereby the test struggles to provide detailed strength readings, as opposed to failure values. This is a common problem with tests carried out on complete blanks, or boxes made therefrom, but is less of an issue in tests carried out on samples extracted from the blanks.

Figure 2:
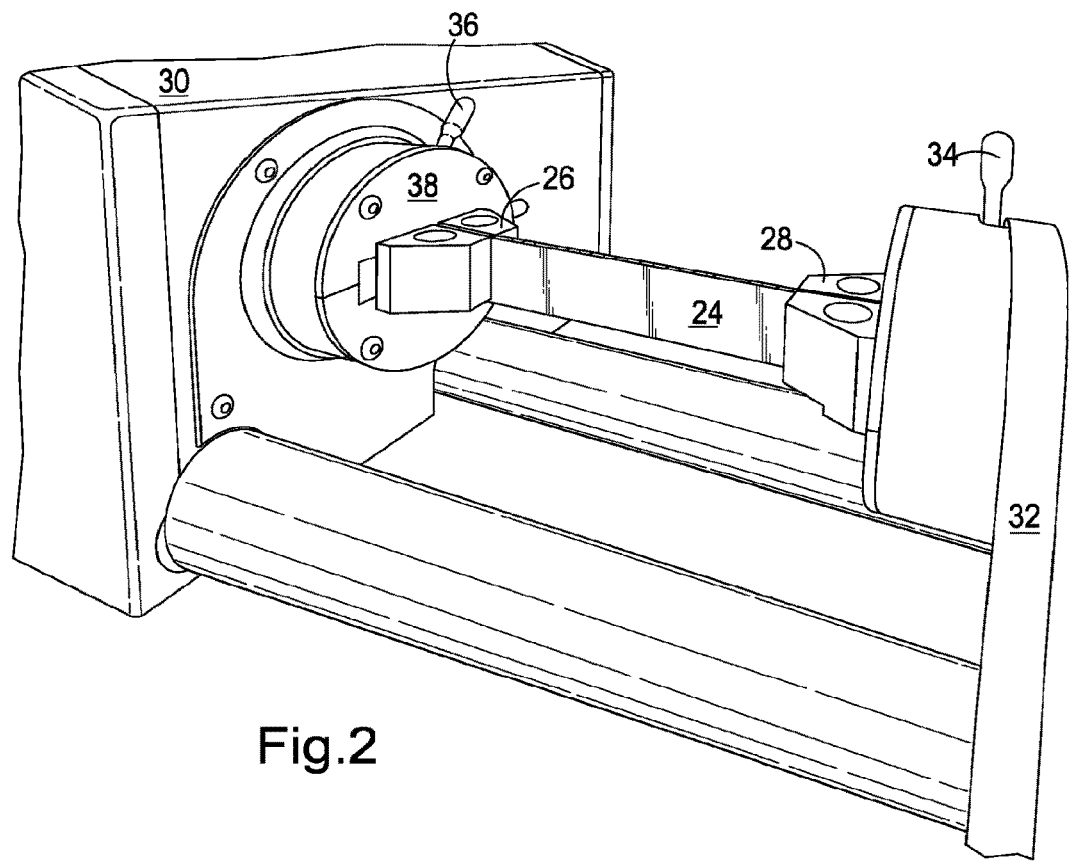
FIG. 2 shows a dynamic stiffness testing apparatus.
Figure 3:
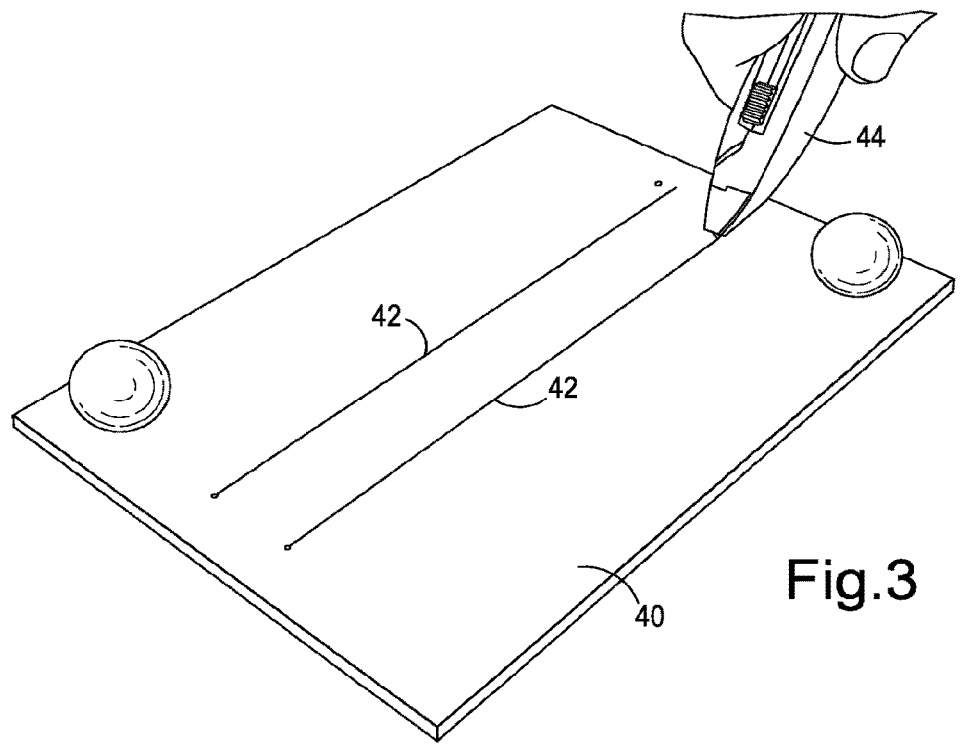
FIG. 3 shows a template cutter arrangement for cutting samples for use in the dynamic stiffness tester of FIG. 2.

Referring next to FIG. 2, such a more reliable test, carried out on a sample extracted from a blank, is illustrated. In this test, a sample is taken from a blank and it is tested by a dynamic stiffness tester or DST apparatus. As also already disclosed above, this apparatus provides a dynamic stiffness reading for the material of the blank, rather than a strength reading for the blank as a whole, this time through a torque loading of that sample. It is considered to be more accurate and repeatable in terms of the provision of a reading as to the quality of the board. These DST tests, however, tend still to be a fairly slow testing process due to the need to cut out the samples from the blank and then to load the sample firstly between two clamps—one at each end of the sample—and only then to perform the DST test.

Although perhaps quicker than the BCT, and more portable since the DST apparatus is significantly smaller than the BCT apparatus, the test procedure, including preparing the sample, may still take minutes, and when carried out on 20 to 30 product runs per day, as would occur in a cardboard packaging production line (each run producing a different product, be that simply a different print run or a different board type, or a different cut-profile), perhaps with multiple tests being required on any given product in order to fine tune the press weights of the conversion apparatus, or other rollers, cutters and folders or the like within the production line, even this faster test is still considered to be too slow to be commercially viable on all product runs. After all, if each test takes two minutes, even a single test per product results in an additional downtime of one hour (two minutes×30 product run changes), and that time will be in addition to the essential downtime created by the roller/material switch-overs between product runs. Nevertheless, the test results are repeatable and reliable and are thus recognised as a good indication of board quality. As such a number of production lines now utilise such tests as a corrugation quality test procedure.

A further problem has been identified, however, with the roll-out of DST tests: due to the need to cut out the samples from the board exiting the production line, it being those samples that are necessarily loaded into the testing apparatus (due to the mode of testing—providing a twist in the sample and then analysing the elastic recovery), there is a susceptibility to variation in the test results due to faults put into the samples by the process of cutting out the samples, or by the process of loading the samples into the clamps 26, 28. For example, too high a clamp force can be provided, and since boards can have different thicknesses and strengths, the regulation or standardisation of that clamp force is not straightforward. Alternatively, if the blade used to cut out the sample is less sharp in subsequent samples, the corrugations can be variably damaged.

The load applied to the guide form or sample template during cutting out of the sample, or the speed of the cutting (or the number of passes of the blade required to complete the cut) can also all introduce variables.

A new test procedure would thus be beneficial to allow both accuracy and speed in determining whether the corrugate meets the standard strength requirements for the type of board that it is.

Eliminating the use of a blade in the production line (i.e. for cutting out the samples for testing) would also be desirable since that can eliminate the health and safety concerns surrounding the use of such blades in the workplace.

One other type of test has also been carried out in practice since it is quick, and it is simply a test or determination of the calliper of a board, i.e. the thickness of the board. That measured thickness can be compared against the standard for that form of board and if the board is too thin (or—less likely—too thick), then the board would not meet the requirements for that board type and would thus be able to be rejected. However, it is recognised that a calliper test is inadequate for determining whether a board is only partially damaged since corrugations tend to have a degree of resilience, whereby they can spring back to a starting thickness if only compressed by a certain amount (albeit enough of a first deflection to cause some damage to the structure of the flutes within the board). A calliper test thus can provide an accurate determination as to whether the flutes are correctly supporting the height or spacing between the faces of the board, but a calliper test cannot determine whether the flutes have undertaken a prior collapse and elastic recovery. That latter deficiency is a problem since if the flutes have undertaken a first preliminary collapse (aka a first failure), the corrugate will not have the same overall stiffness and strength characteristics as if the flutes had not undertaken such an initial collapse, rather like fibreglass crash helmets—they are not as strong after a first impact.

Figure 10:
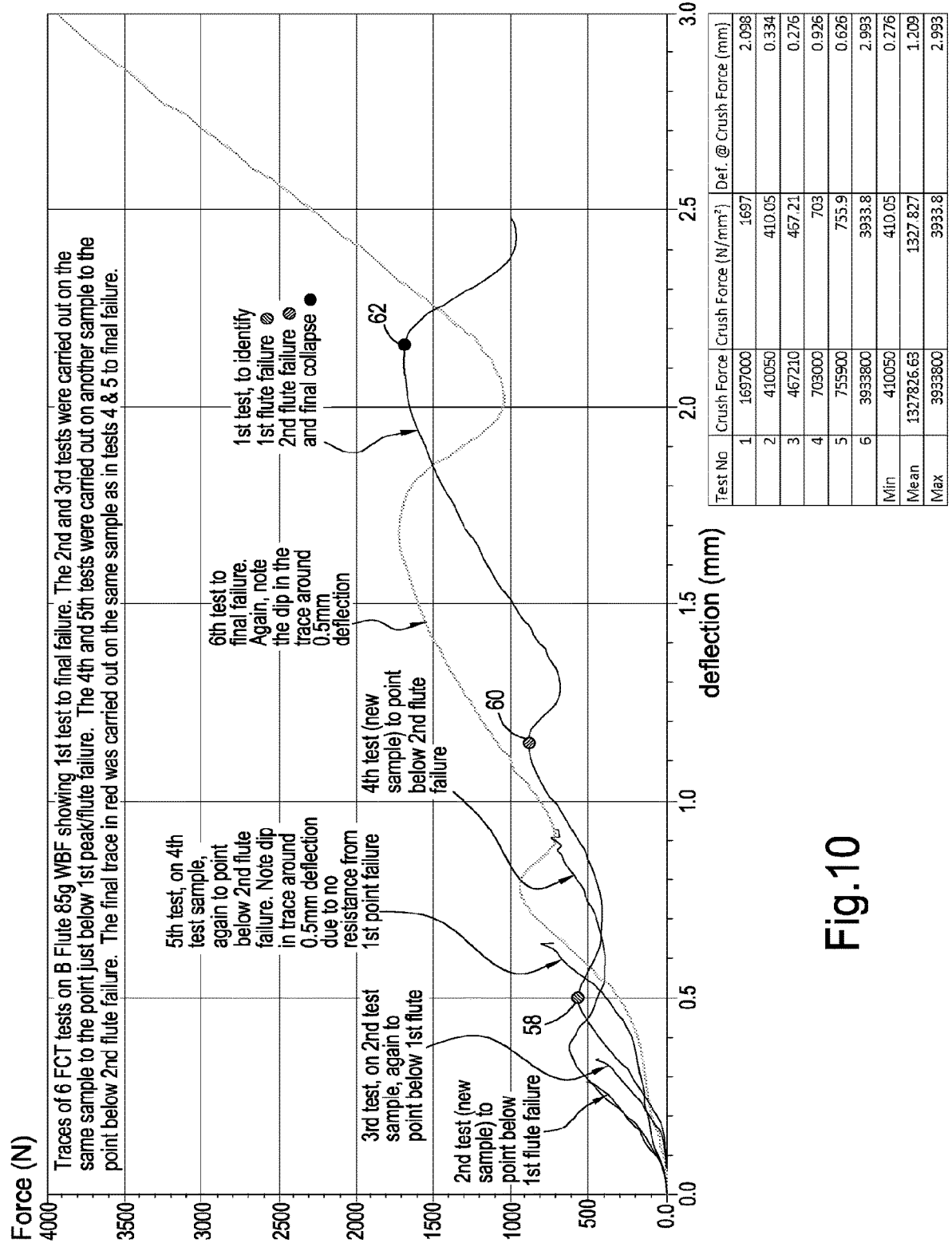

This imparted weakness in the flutes following a first partial compression can be seen from the deflection/load traces in the graph of FIG. 10, where repeat tests were carried out on various samples, and each to different degrees of failure, so as to show the different trace characteristics in such circumstances.

The tests carried out are numbered from 1 to 6.

The first test was carried out simply to illustrate the existence of first, second and third point failures. For the general form of these failures, see FIGS. 35 to 38, which represent the mode of each of these three failures by providing a generalised illustration of the flute form in section at each failure point.

The three point failures are represented by the three peaks 58, 60, 62 in the trace, with the first peak 58 corresponding to a first flute failure, as shown in FIG. 36. This is where the crown of a first of two opposing flutes within the waveform of flutes fails (or buckles). The second peak 60 then indicates a second flute failure, corresponding to FIG. 37 where the crowns of both the top and bottom waveforms of the flute collapse, fail or buckle. The third peak 62 then indicates a final collapse of the board. In this failure, the walls between the crowns also start to collapse, fail or buckle. See FIG. 38.

The second test was then carried out on a new sample with no damage. Its trace is shown to be displaced along the X axis relative to the first trace, but this just represents a different start point therealong—the forces measured during the loading characteristics are otherwise clearly similar to the first trace.

As can be seen, in this second test, the loading was commenced, but it was also ceased prior to the degree of compression causing a loading force corresponding to that first failure point 58, i.e. the loading peaked at about 500 N, whereas the first point failure occurred in the first trace at a load of about 600 N. As such, a degree of flexure was undertaken by the flutes, but the flute did not fail.

Upon releasing the compression, the board elastically reassumed its starting thickness.

That same sample was then tested again in a third test (a second test for that second sample) and the trace can clearly be seen to be repeating the same curve, albeit shifted again along the x axis (by about 0.1 mm) in the graph due to it again having a different start point (e.g. since the elastic recovery was not perfect, whereby there may have been a slightly smaller calliper—perhaps the 0.1 mm mentioned above).

A fourth test was then carried out on another new sample (first test for this third sample) and that sample was tested through the first failure point but was ceased from further deflection just prior to the second failure point—at a deflection point above and beyond the load point of the first failure point 58, but less than the second failure point 60. This was done so as to allow a subsequent test to be carried out on that same third sample, but this time with that sample now being a part failed sample.

The fifth test is the second test on that third sample, i.e. a test on a part failed sample, and as can be seen the first peak failure 58 simply does not occur, and the trace initially follows a much lower path towards the second point failure. Then the trace simply flows up towards the second point failure 60 (although the compression of this third sample was again not taken to that second point failure 60.

The sixth test was then again carried out on that third sample, but this time it was instead taken to a final failure. The trace is again slightly shifted due to a different start point, but it initially generally follows the trace of the fifth test.

It can also be seen in this sixth test trace that the loading required for the second point failure 60 is roughly the same as in the first test (around 900 N). Likewise the load for its final failure was also similar to the first test (around 1700 N).

The end of the trace going upwards simply indicates the full compression of the board whereupon the loading increases as the plates of the test apparatus push against each other through the compressed corrugated sample.

From the above it is clear, therefore, that observance of the loading characteristics in response to initial deflections can give an indication as to whether the board has already undergone a first point failure. Such a failure is the type of failure that might be inflicted upon a corrugated board during the corrugation process or during the conversion process, e.g. if the roller gaps or the roller pressures are set incorrectly, but yet would not be detectable by a calliper test. The present invention therefore tries to detect such a failure so as to allow a supplied board to be certified as being in compliance with the requirements of the board type being supplied.

Due to the non-existence of the first failure point in a damaged board resultant of a first flute failure, a comparison of the trace or force versus deflection curve allows such a determination as to whether or not a board that has undertaken processing in a roller based converter or corrugator has been damaged by that process or not. If it exhibits the initial strength characteristics of a non-damaged board, it will follow a path towards a first failure point, but if it has been damaged by that processing so as to have already undertaken the damage to the flutes, it would instead exhibit a lower loading characteristic upfront before reverting towards the second point failure point.

It is therefore possible through comparison of test data on a live sample, and comparing it against the expected test data for a pre-tested sample of a non-damaged form, to determine in a non-destructive test whether a sample is damaged in that way, or not.

Referring next to FIG. 4, a test apparatus that can be used to produce sample data for a look up table on undamaged products is shown. In this example, disks of typically an 80 mm diameter are cut from boards known to have not been damaged, and test data can be obtained therefrom whereby the data behind the curve corresponding to that of the first test in FIG. 10 can be obtained for all different forms of board that are to be produced by the production line. This can include test data for boards made from various different top sheets, different bottom sheets, different corrugations (shapes, frequencies and amplitudes), plus also various different corrugation/board thicknesses, and ply numbers. This data can then be provided for a look-up table for comparing against live data on actual product of the production line, e.g. for a live product.

Figure 5:
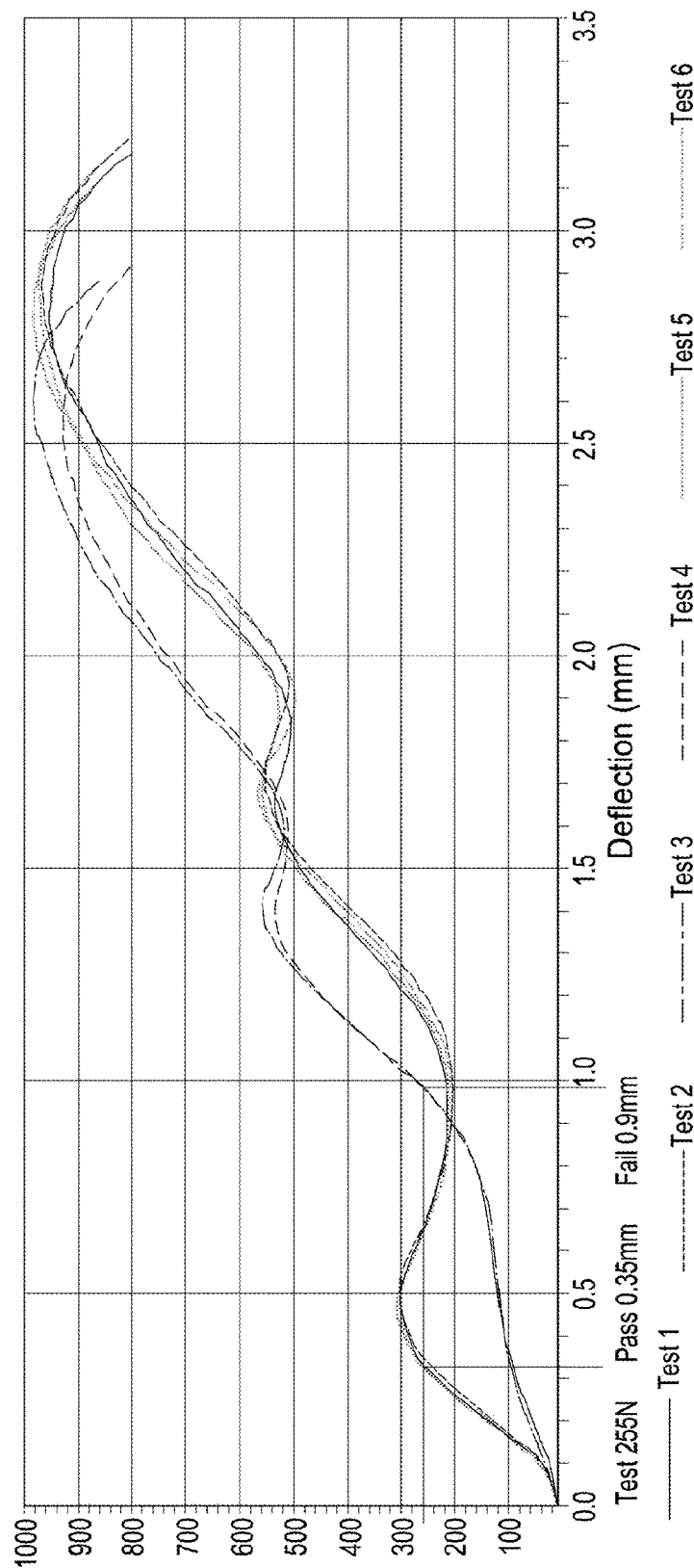

Referring next to FIG. 5, six traces of separate tests through to failure are shown, with four of them being on undamaged stock and two of them being on damaged stock, and thus following a different path towards the second failure point—the first point failure does not occur. As can be seen, the undamaged stock have traces that follow a path with three clear inflections, each representing one of the three failure points previously described. The other two traces have only two clear inflections.

Figure 6:
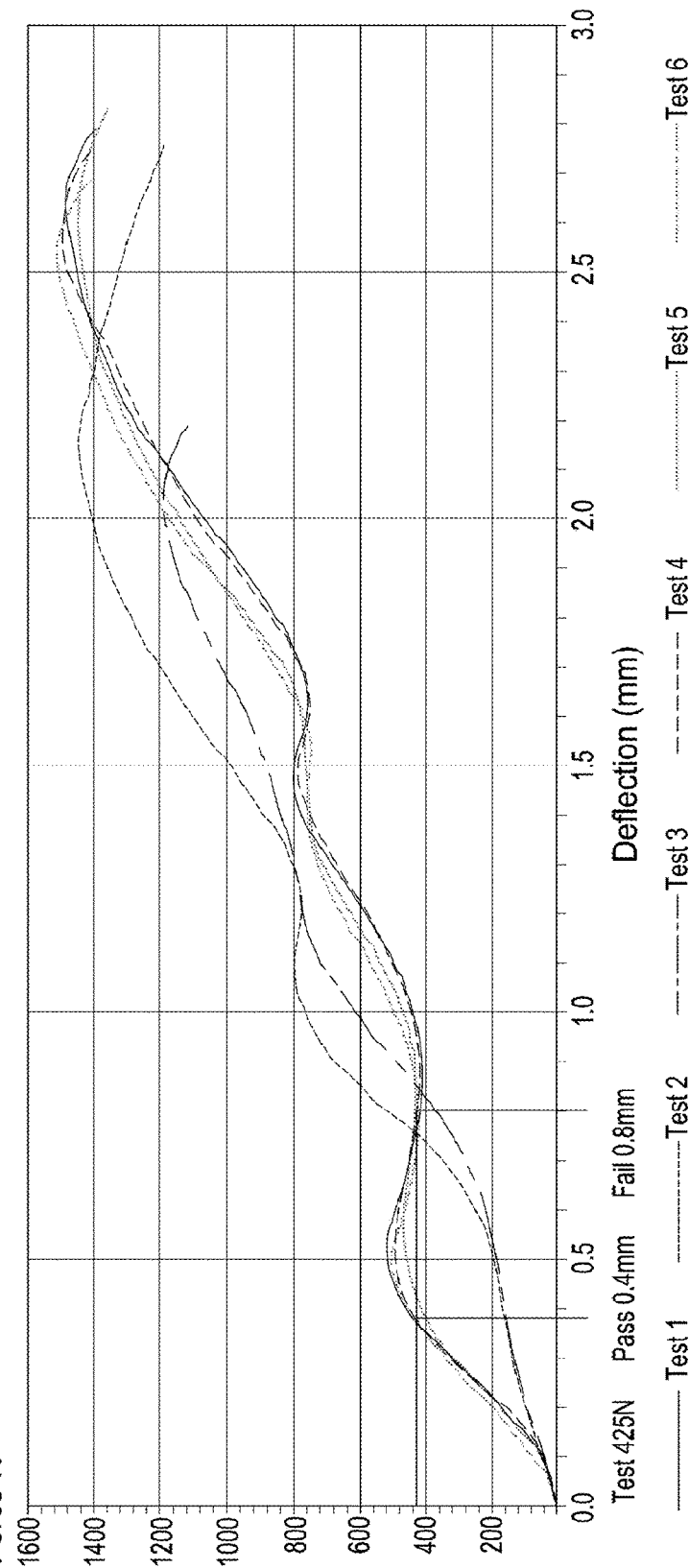

FIG. 6 then shows similar tests on a different type of board—in which the corrugate is made of a more stiff material. In this test, again four of the traces follow substantially the same form whereas the other two clearly do not exhibit the first failure point inflection. Damage again can thus be identified simply from an analysis of the early part of the curves (or the early response to deflective loading).

Figure 7:
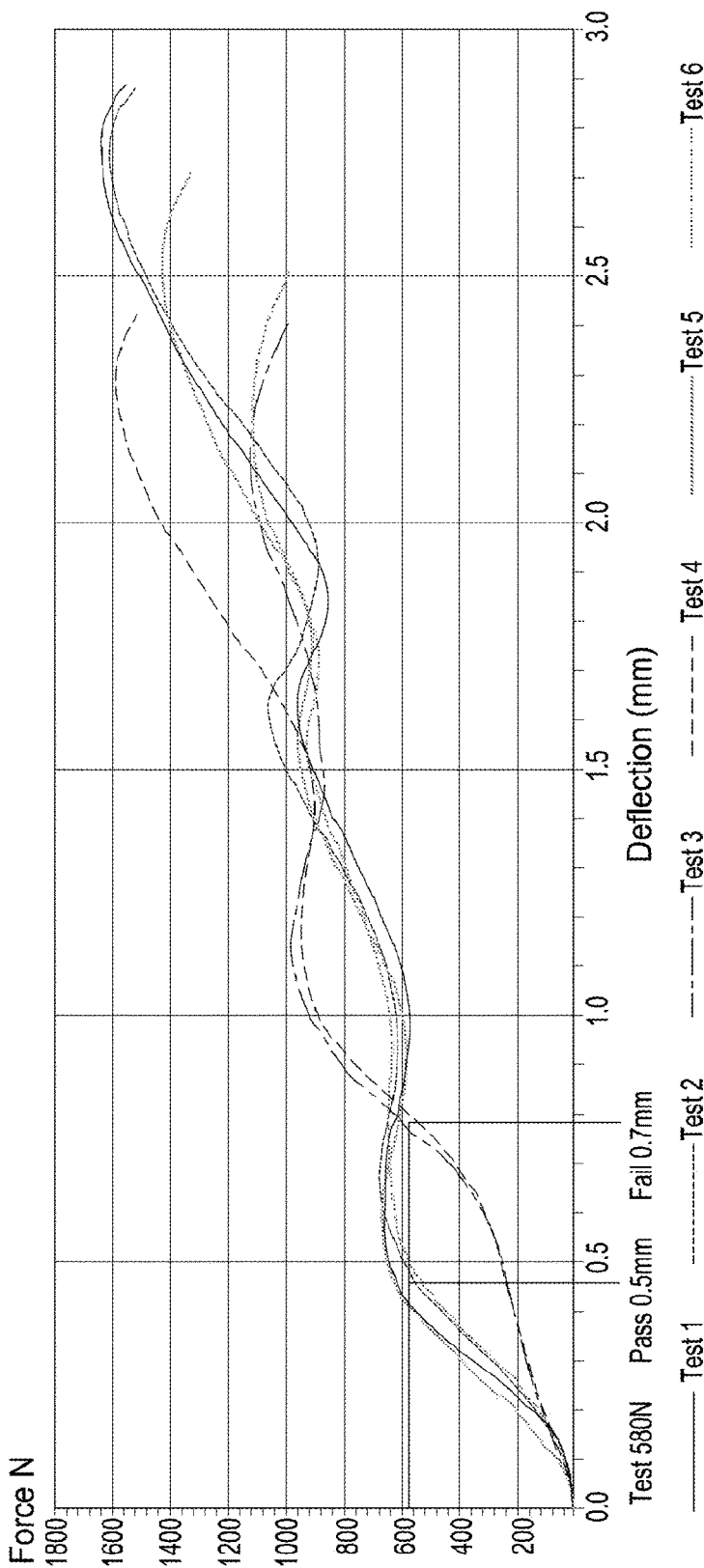

FIG. 7 then shows six further traces, again where four boards exhibit the three failure points whereas two only exhibit two. In these samples, a thicker flute material is used and a greater variation in the final failure point is exhibited. Nevertheless, the first failure point is still adequately repeatable to allow a determination to be made since there is a distinct difference in the trace of the two damaged boards compared to the non-damaged boards. Thus again a study of the early load response to deflections can indicate whether a board has been damaged.

Figure 8:
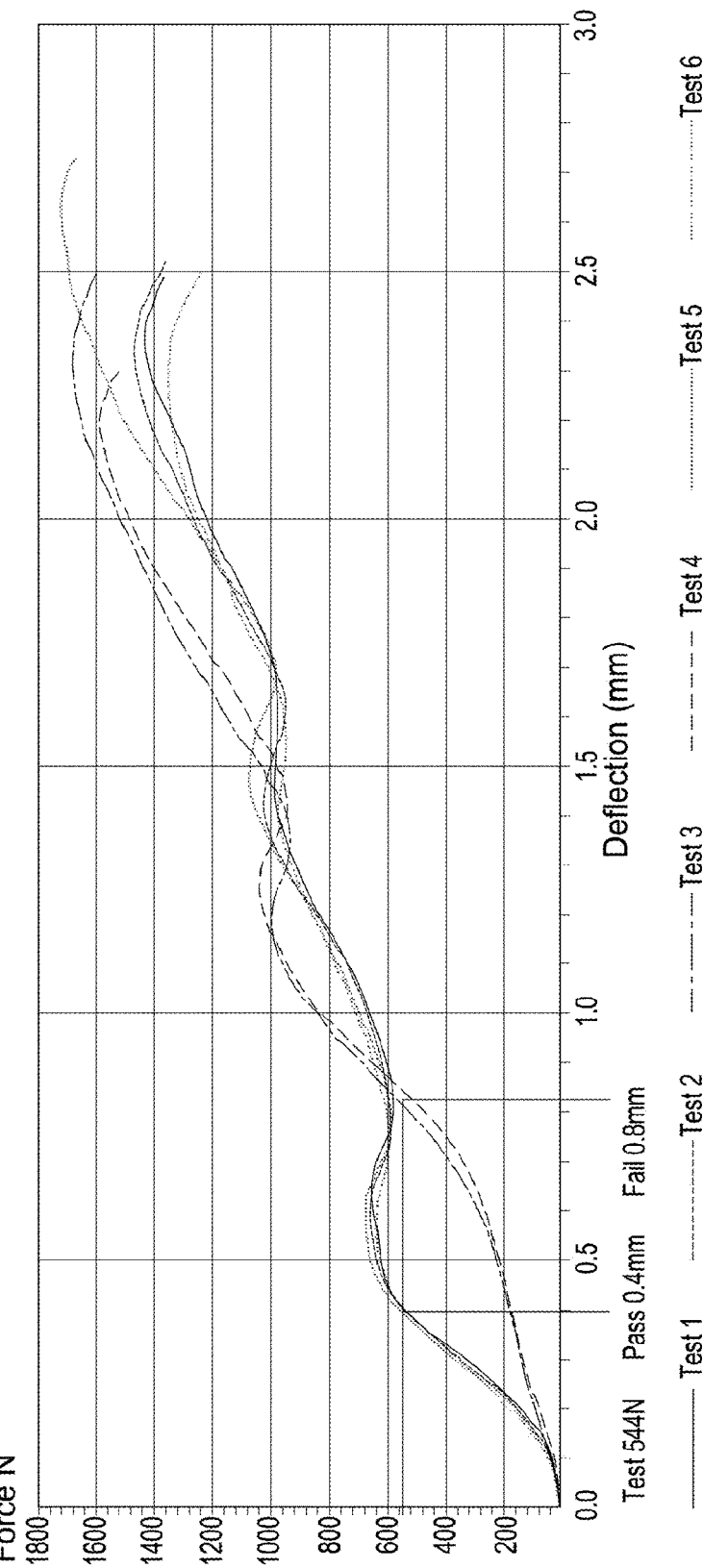
Figure 9:
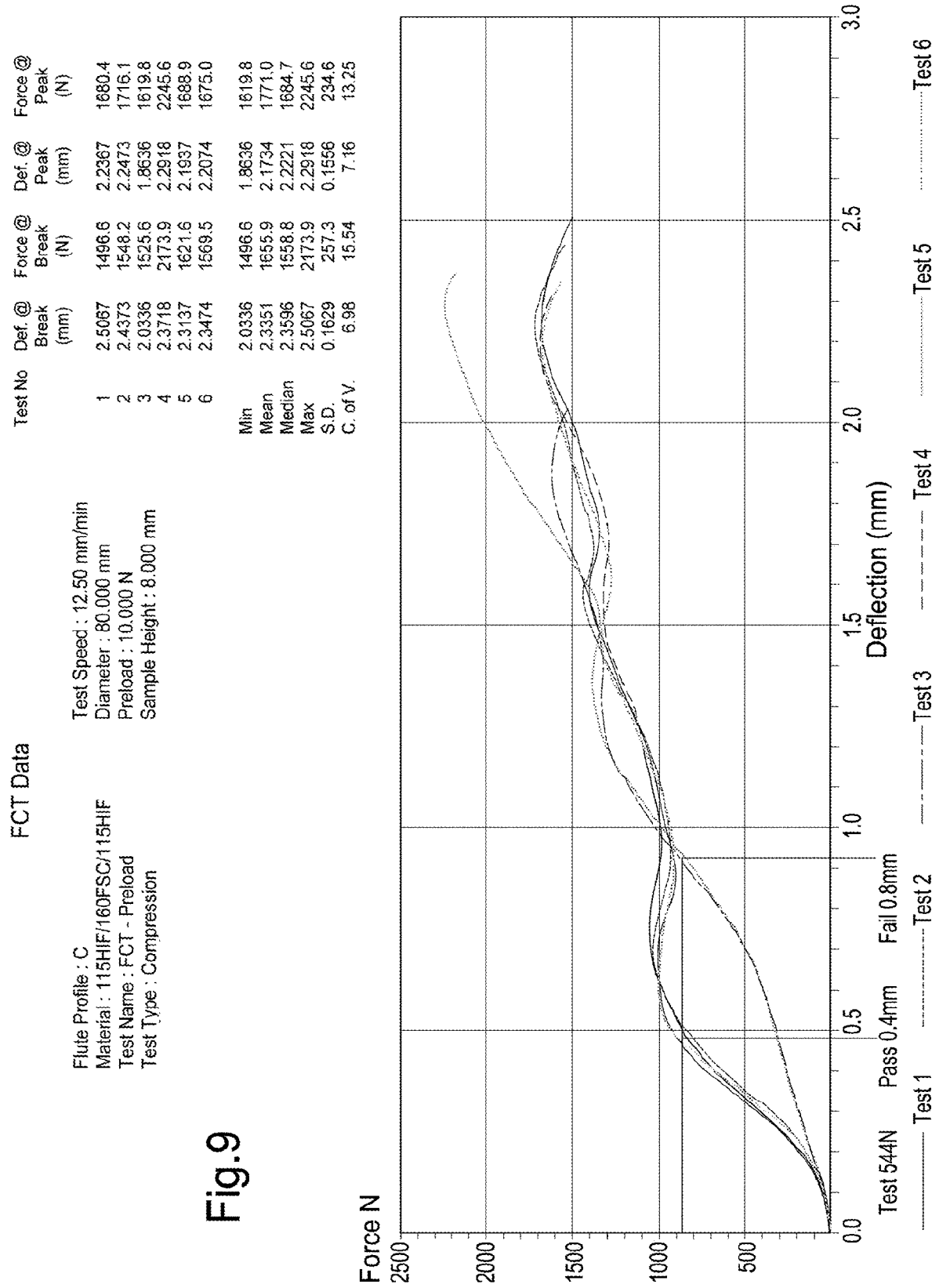

FIGS. 8 and 9 show yet further traces for boards made from the stiffer flute materials and yet again the existence of the first failure point in a board that passes the test is readily apparent, when compared to the two boards that are damaged, whereby a pass or fail of boards can be achieved based upon the initial response to loading.

It is clear, therefore, that by looking for the compression resistance (herein measured in Newtons) of a live sample to a given deflection and comparing that to the expected response to such deflections, and perhaps looking at that at a point between, for example, 50 and 90% of the expected first failure point, the quality of the fluting can be determined. Likewise, the deflection resulting from a fixed loading can be measured and compared with expected deflections for that loading, again at say between 50 and 90%, or more preferably about 85%, of the first point failure, can provide an indication of flute status. If the board passes the test, then the fluting is in a correct or acceptable condition whereas if it fails the fluting has been adversely damaged, for example by the processing of the corrugate.

The present invention initially relates to that test procedure since it allows a quick test to be carried out since it is not necessary fully to collapse the corrugate to undertake the test and secure a reliable reading. Preferably the test is carried out directly on the board as it exits the production line, either before or after the conversion thereof, i.e. without cutting samples from that board. The test apparatus thus has a gap or slot for receiving an edge of a board.

In view of the faster test, it is also possible to have the test carried out beside the production line whereby an operator can perform tests and fine tune the roller pressures so as to avoid damage to the board during production of the board or conversion of the board into the respective blank's further customer. This can even be done multiple times a minute since only a very small deflection is needed to get a test result—typically less than 1 mm or even less than 0.5 mm.

The inventors have also recognised that a single test on a width of corrugate passing through a corrugation machine or a converter is not always going to be adequate or accurate for a board as a whole since there can be variations in the wear or set up of the rollers within the corrugator or converter. For example, one edge of the board may be more compressed than the other, or the middle may be compressed more than the edges. This can occur, for example, if the roller has worn, e.g. so as to be tapered along its length, or even if it is just misaligned slightly. The present invention therefore also provides a method in which multiple tests are carried out across the width of a single board. With the prior art methods, since samples had to be cut out from the board, this would then involve cutting multiple samples from the width of a board, thus further lengthening the testing process. The present invention, however, achieves the full multiple test process without cutting such samples from the board, which saves time since cutting out samples slows down the testing process perhaps to an unacceptable level. According to the present invention, therefore, it is desired that the board be tested intact, rather than samples being cut therefrom for testing. It is also preferred that the test preparation and performance cycle be shorter than 20 seconds.

In a preferred arrangement, the intact board or blank is tested in multiple locations thereon. For example, for a blank for a box with four sides, the test may be carried out on all four panels for forming the sides of the box. If there are more sides, then more tests may be appropriate, although testing every side is not essential. Likewise if there are flaps or other significant panels, they too might be tested. Again, however, that is not essential.

It is preferred that the test preparation and performance cycle for each of these tests be shorter than 20 seconds. Collectively they may take longer than 20 seconds.

Preferably the present invention involves testing a board in more than one location and more preferably in four or more locations.

The board may be a finished blank or it may be a cut board or width of board from the corrugator, i.e. prior to insertion through the converter, or a part formed blank or board sitting on the feed tray of the convertor unit. Tests on the latter two can provide a reference for the post converted, or finished, blank. Then, if the conversion machine provides damage to the blank, this can be later identified—by a subsequent test on that earlier blank after the conversion process. The conversion machine can then be adapted or its pressures can be lowered, to correct or remove the set-up error therein. However, if the first test shows instead that the corrugation machine is causing the damage, then the corrugation machine can instead be adjusted.

Since the machines within the production line tend to have button controls for adjustment of roller pressures and the like, by having the testing apparatus beside the control apparatus for the corrugator or the converter, rapid testing of the boards or blanks combined with the quick and easy adjustment of the roller pressures can allow the blanks coming out of the converter apparatus rapidly to be fine-tuned so as to provide desired results.

It has been found that with the present invention, more than three and maybe four or more tests can be carried out, with adjustments to the machinery where needed, per minute, with the test itself perhaps taking just 3-6 seconds.

It is preferred that the tests are carried out in a controlled environment. This would include the testing that is carried out for populating the look-up tables and also the testing carried out at the production line during the manufacturing process. Preferred environmental temperatures in most cardboard packaging industries are 23° C. and 50% relative humidity, +/−1 degrees and +/−2%. The controlled environment provides a foreseeable or repeatable characteristic to the board, which can be especially important with wood or cellulose fibre based corrugates.

As already indicated, by locating the testing apparatus adjacent the production line, product can easily be taken off the production line while the production line has been halted. That product can then be tested and then the production line adjusted if necessary. Then the operations of the production line can be reinstated into production mode to throw out the next product for testing (e.g. if an adjustment was previously made) to check the modified product for conformity with the required standard.

Since the test is carried out on the product, rather than a sample cut therefrom, or even on a reshaped product (e.g. an assembled box therefrom), and since the test is only looking at the initial response to loading, the test procedure is fast enough to allow multiple tests and production line adjustments, and resumptions of production, to be conducted in a minute, or in the time previously taken to do a box crush test or even a dynamic stiffness test.

The quicker test therefore reduces down-time between production runs, thus increasing productivity. It also allows production line damage to be reduced, thus allowing greater efficiency in the use of materials—chosen materials can achieve more consistent strength characteristics in the resulting corrugated sheets/products, and since the method can identify damage caused by the production line, and thus then eliminate it in the remaining product production for that production run, a smaller safety margin on strength can be used by the manufacture for the customer, thus allowing lighter packaging to be provided while still consistently providing the required strength performance demanded by the customer.

These weight reductions can also reduce environmental damage since the packaging will use less raw materials, and can also reduce transport costs since there will be less packaging to transport/recycle.

Referring next to FIG. 11, a first embodiment of testing apparatus of the present invention is shown. It comprises a support surface 46 onto which a board to be tested can be located, a pressure plate 48 for imparting the test pressure onto the board thereunder, and a frame 54 for supporting the pressure plate 48. In this embodiment the frame additionally supports the pressure plate's drive rod 64, the force sensing displacement mechanism 56 and the load sensors or senders 52 for sending data to a computer 66 via a cable 68 (in this case a USB cable to a separate PC/laptop).

The apparatus also comprises a power unit 70 provided to supply the power to the force sensing displacement mechanism 56 and the load sensors 52. This embodiment also has a second power unit—provided since there are components that operate at different voltages, or since there wants to be a separation in the power supply between the drive motor and the sensors to avoid interference. However, a single power unit might instead be provided if preferred to reduce costs.

The support plate 46 in this embodiment is formed of a single component with its legs 72—for standing the test apparatus on a table. It is also possible for it to be an integrated design with the frame 54.

The pressure plate is significantly smaller than the support plate in this embodiment. However, different arrangements are also possible, as illustrated in FIG. 1 or 4 for example (where they are the same size). Making it smaller than 10% of the size of the support plate is preferred, however. Having a small pressure plate allows the drive unit for the pressure plate to be small, yet still capable of providing an adequate pressure onto the board in the test apparatus. Having a large support plate, on the other hand, is preferred since it can then still offer a stable support surface for the board being tested—the board will have a reduced tendency to rock on the support plate—a potentially important benefit bearing in mind that the board may be being held within the test apparatus by an operator.

The power supply 70 may be connected to mains power through further cables 74 and may thus comprise a voltage converter.

In this embodiment, the force sensing displacement mechanism 56 is in the form of a moving coil actuator, or a voice coil, and it is preferred that it is able to provide displacement measurements up to an accuracy of at least 50 micrometres, or more preferably 10 micrometres, or better still 5 micrometres or 1 micrometre. Accuracies up to between 1 and 0.1 micrometres may in some instances be beneficial too, although generally this would not be essential. About 5 micrometres is the accuracy of the preferred device.

For small pressure plates as discussed above, it is preferred that the drive unit be able to apply loads of up to 100 N, or 150 N or even 200 N. Larger forces become non-essential due to the small pressure plate. A preferred device provides loads of up to 185 N. This is typically adequate for testing apparatuses having a pressure plate 48 in the form of a 25 or 20 mm diameter disk. The pressure plate may of course be larger or smaller than that. Likewise the force capability of the drive unit may be larger or smaller than 185 Newtons.

Since the fluting is not needed to fail completely during the test, and since the load area is smaller, smaller loads are required than in box compression tests, or in the lab equipment used to test the 80 mm discs of FIG. 4.

One style of power unit that is suitable for the present invention's testing apparatus is a moving coil actuator. Manufacturers of such equipment include SMAC. Such devices can be linear and linear/rotary actuators, and two possible model numbers are the LAL 300 and the LAL 500, both by SMAC. Others include the LAL 95-015-85 unit by SMAC. Preferably they have a high speed single axis controller. A suitable controller may be the LAC-1 controller by SMAC.

It is preferred that the arrangement will provide a displacement measurement and a load reading for that displacement with a stroke length of up to 15 mm, 25 mm or 50 mm, whereby it is perfectly adequate for testing corrugated sheets—such sheets are rarely thicker than 10 mm.

Referring next to FIGS. 13 and 14, a modified version of the testing apparatus is shown. In this modified version, the computer is incorporated into the housing itself and thus there is a screen on the front of the testing apparatus. This screen is a touch screen to allow user interaction for controlling the test procedure.

As also shown in FIG. 14, a slot is provided into which the board can be slipped for the purpose of testing. That slot 76 is preferably at least 10 mm wide so as to accommodate board thicknesses commonly found in the corrugated business. Wider thicknesses for the slot may also be used if appropriate for larger boards to be sampled. The slot is shown to be of a fixed width, although it might be adjustable if desired, e.g. for securing a board within the slot for the duration of a test. Note though that such a securement is preferred to be absent since it might become a cause for damage to the board.

The slot arrangement is beneficial since it allows an edge of a board to be presented very rapidly into the testing apparatus. A slot can also provide a safety guard mechanism since a slot is restrictive in terms of the access it provides, without hindering the test apparatus' ability to receive a corrugated sheet quickly. For example, the slot will resist the insertion of the operator's fingers that hold the sheet since the fingers are unlikely to additionally fit within the slot, but is wide enough to readily receive the board's edge.

In use, the touchscreen 78 may have numerous software icons or buttons on the screen, which buttons or icons 80 may vary from mode to mode of the testing apparatus. In FIG. 13, an initial mode is shown in which there are various option buttons. For example, the type of test to be carried out can be selected or the type of board to be tested can be selected.

It is preferred that the machine be connected to the production line's network so that it can be automatically provided with details of the current production run, or so that it can upload them from a database, e.g. from a product order number. However, the details might instead be user selectable on the screen, e.g. via drop-menus or an input device such as a keyboard (virtual on screen, or a separate hardware one).

FIGS. 15 to 19 show further screen options, e.g. for later test steps.

Figure 15:
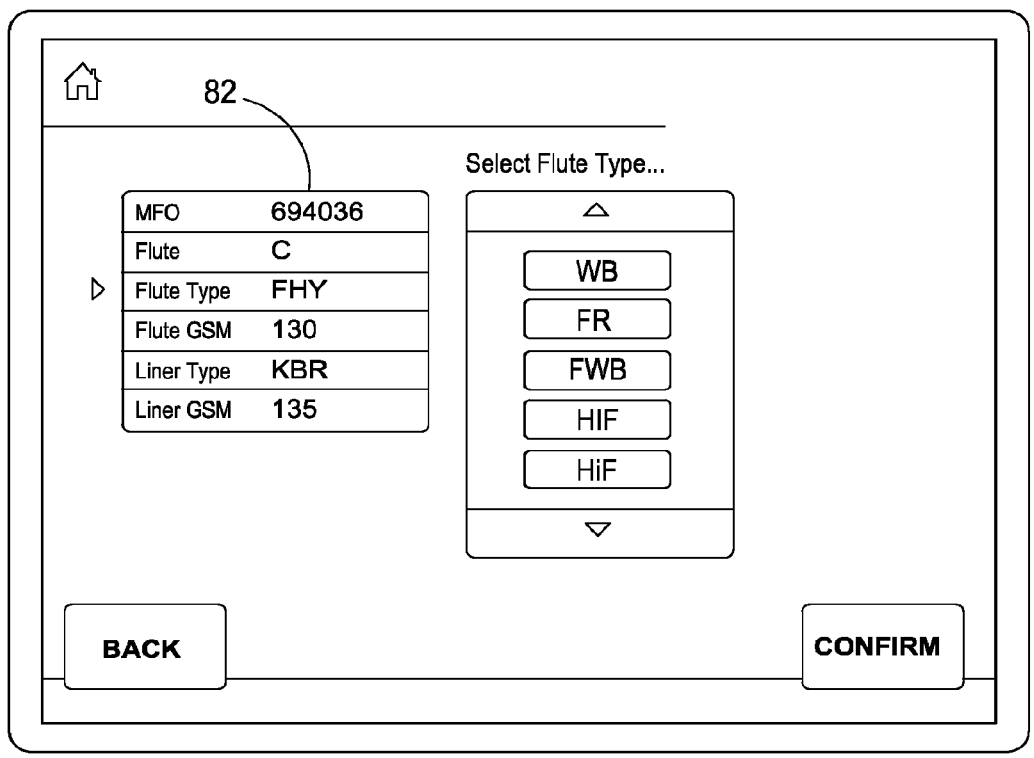
Figure 16:
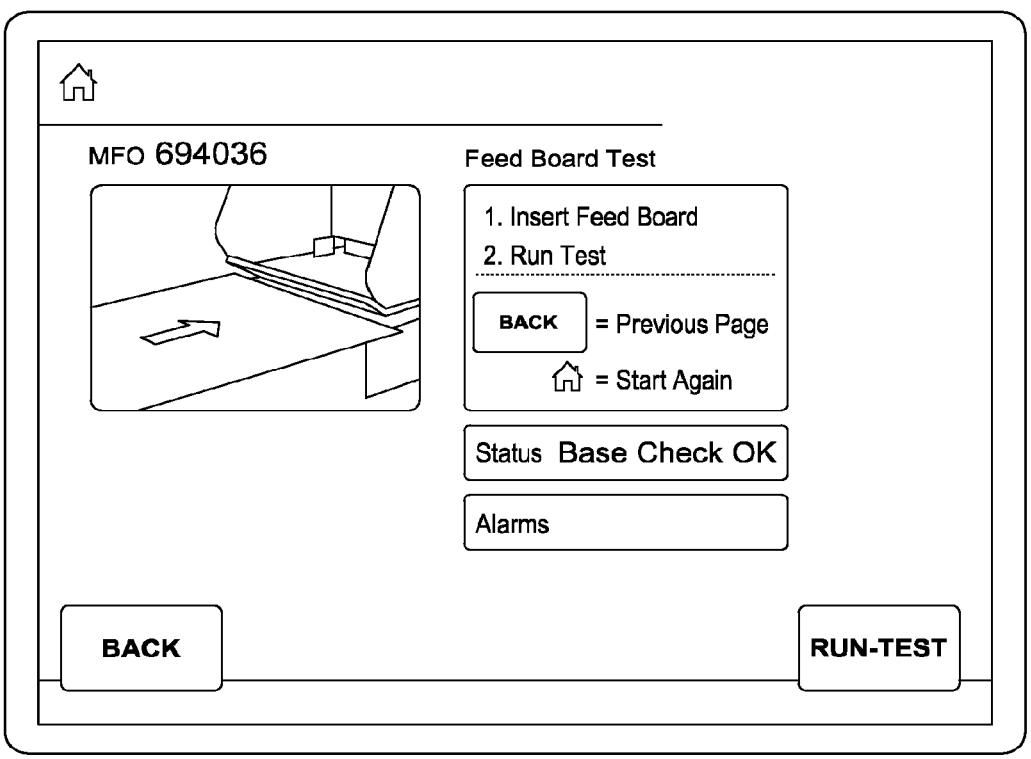

The screen of FIG. 15 allows the materials of the board to be indicated or set. The manufacturing order number (MFO) is indicated at the top of a first table 82, and in this table there is also indicated the designated details of the type of board expected for that order. In this example there is a board with a type-C flute, made from a FHY type of material having a weight of 130 grams per square metre (GSM), and with liners top and bottom having a KBR or Kraft type and a weight of 135 grams per square metre.

In a second table to the right of the first table, other options can be selected if desired from the presented drop-down list, such as the flute type in this instance. For this purpose, the entry "Flute Type" is selected on the left hand table, as indicated by the arrow thereagainst. Being a touch screen, this may be by pressing the relevant box of the table 82 with a finger. Thus a different flute type can be selected from the drop down list on the right if appropriate (e.g. if the production run is modified from the default for any reason).

Once the type of board is indicated on the screen and it conforms with the board to be tested, the user can press the confirm button to move to the next stage.

In this embodiment, a reference test is first to be undertaken and in this instance that is in the form of a feed board test. It is preferred that this occurs for each production run, or whenever the corrugator is adjusted (rather than just the conversion machine). For this purpose, a board from the output of the corrugator, or more preferably from the feed end of the conversion machine, i.e. prior to a pinch point by a feed roller of the conversion machine, is removed and inserted into the test machine so that the test can be run thereon. This is to ensure that the corrugator is producing correct board and that it does not need to have its roller pressures updated or changed. This reference test is also beneficially used as part of the overall compression test—after the conversion of the board, as will be described in further detail below in relation to a preferred embodiment, since it provides a calliper for the board prior to feeding into the conversion machine.

In the process of testing, the deflection and force readings are taken and are compared against data from a look-up table, with the normal readings for that board type having been determined previously under laboratory conditions. Assuming that the feed board meets those standards, the boards from the convertor, i.e. converted board or product, can then be tested at the next stage.

Figure 17:
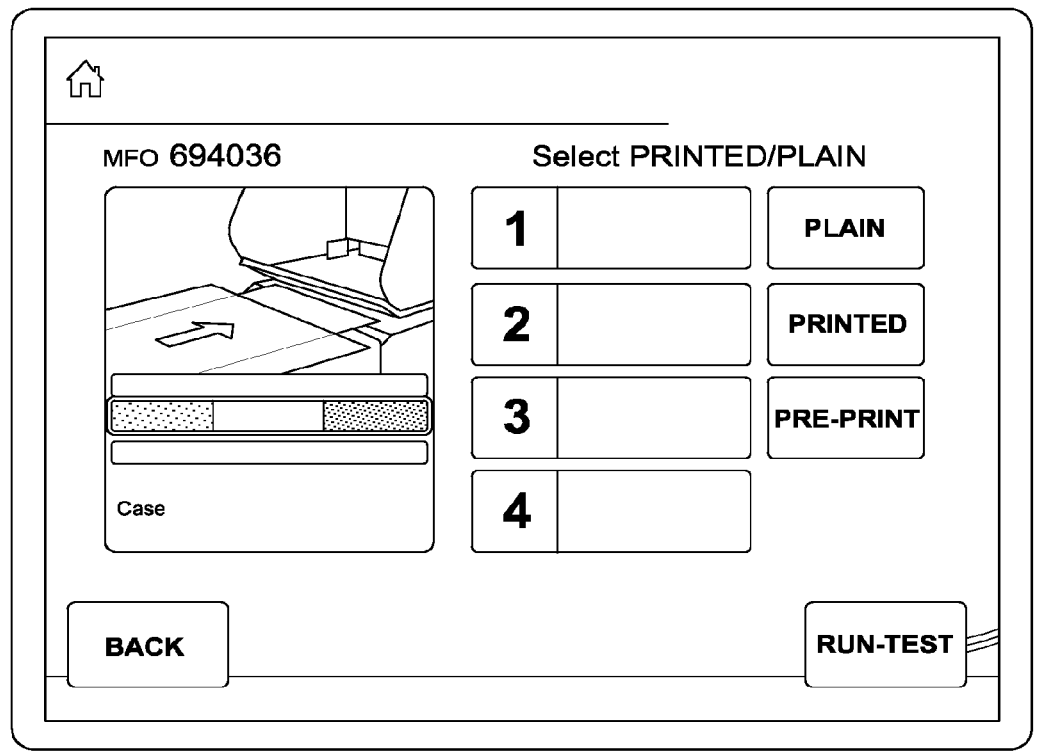

FIG. 17 shows a preferred next stage screen, which is ready for receiving the blank. That blank might be printed or plain (or pre-printed) and a button can be pressed on the screen to select this. This is a preferred option since the type of printing on the blank can change the characteristics of the board as a whole due to it potentially being a further layer on the board, e.g. in the event of use of pre-printed cover paper, or it can mean that the board has undertaken a further compression cycle in the event of an inline printing process involving the use of print roller. Then the tests can be gotten underway.

Figure 18:
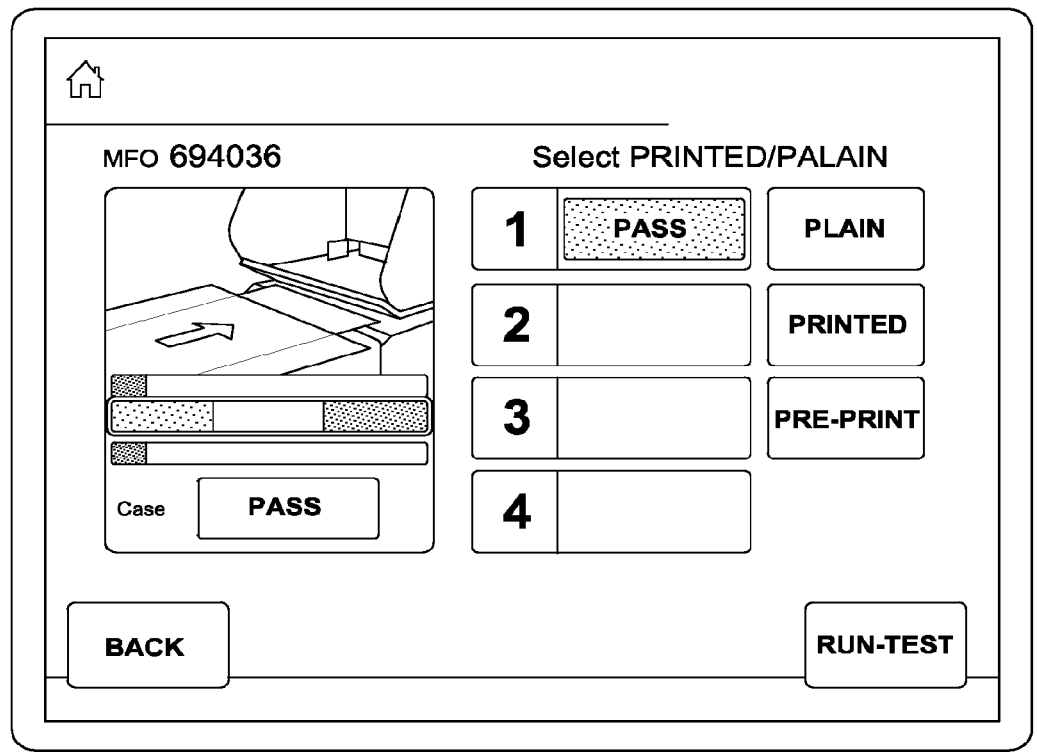

As shown in FIG. 18, a first area of the board has been tested and it has passed. In that test, the board was inserted in the slot and the "run-test" button was pressed. The pressure plate then pressed down on the board to squeeze it against the support plate and the apparatus simultaneously took deflection/loading readings, perhaps at a 85% deflection point relative to the known "first point failure point" for that board type (as predetermined under lab conditions). 50% to 90% would also be possible. Before the loading, however, a soft landing calliper was taken to determine the pre-compression thickness of the board. This can be compared with the similar calliper taken for the board when it was a feed board, i.e. prior to conversion.

Figure 19:
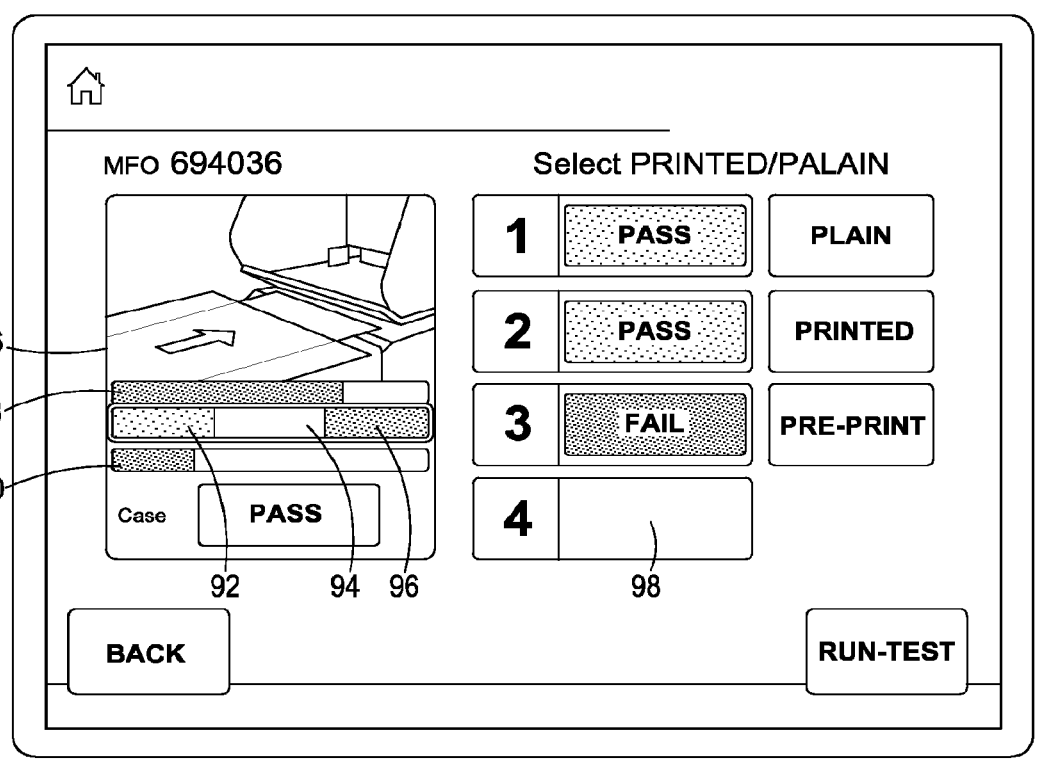

Then in FIG. 19, second and third sections have been tested. The second section has passed but the third section has failed. For the purpose of achieving such a result, the tested board had been deliberately damaged (e.g. compressed with fingers) in the area of the third test so as to create the fail result. In practice, a fail would generally only occur if the production machinery caused the damage.

To improve the test process, rather than having a single fail cause the board as a whole to fail, a rule can optionally be applied, as here in this example, to help the test process to ignore localised failures. For that purpose, a single fail is generally not enough to fail the product.

As can be seen in FIG. 19, there is also, below the picture area 86 to the left, a traffic light system for indicating whether the board or blank as a whole passes or fails. This, although optional, beneficially works together with the multiple-test test procedure. In this case, despite the third section's fail, the product is still overall a pass (although there is a fourth test still to do), since the top line 88 of the traffic light system—which records the overall average score required in order to create a fail—a figure that can be absolute for a given board type, or set individually for an order for meeting customer demands (some want greater strengths for a given board, whereas others are not too worried about the board's strength)—is still not reached by the running-average score 90. Indeed, that running average score 90 is actually still overlapping the green traffic light area 92 since the first two tests had good results, and the third was a borderline fail.

If the average score following the fourth test was then to enter the amber warning region 94 (or even the red region 96 in this example since the top line (or the pass bar 88) defines the point at which failure is to occur), then an overall warning or fail would occur, as appropriate.

The present invention therefore not only does tests but can also provide average score tests. This is beneficial since it allows a localised fault not to cause the blank as a whole to fail.

Further, a customer or manufacturer can specify the conditions for a fail (average fail/singular fail, amber fail, red fail), whereupon there is added flexibility. This then allows a manufacturer to avoid failing a board that is otherwise going to be perfectly acceptable to a customer. This can then speed up production runs even further, or even potentially prevent a large volume of paper to be wasted compared to the situation where the provisional materials specification cannot meet the required customer specification, which clearly offers an environmental benefit.

Figure 20:
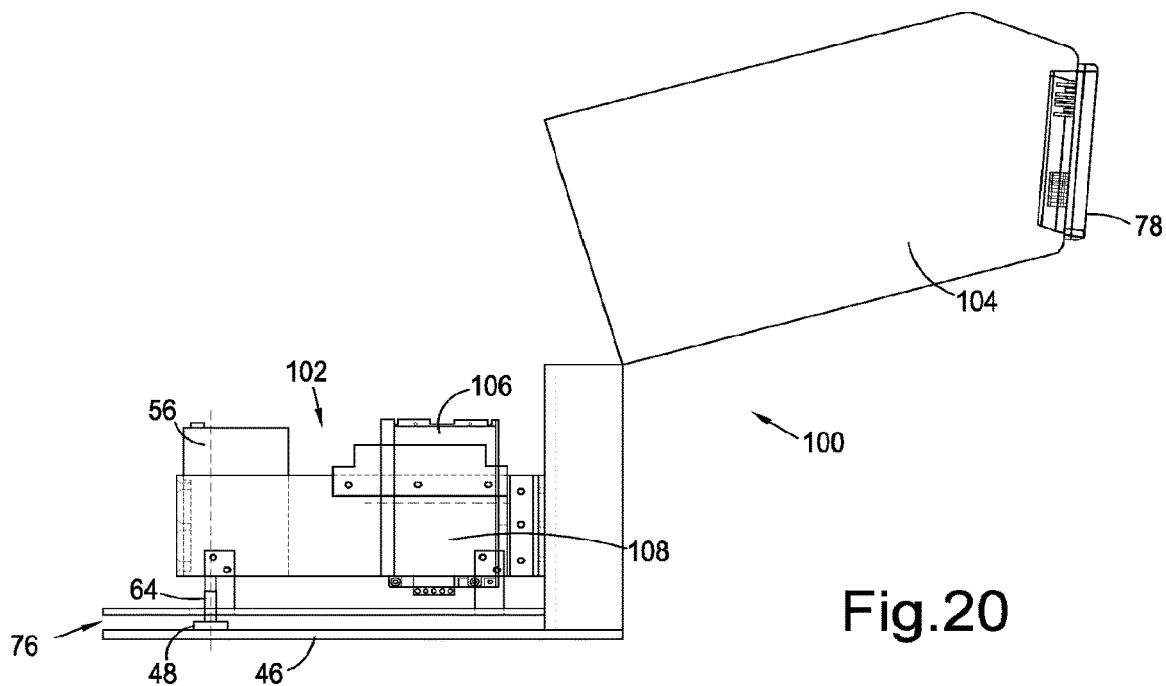

Referring finally to FIGS. 20 to 34, a preferred assembly for the flute integrity tester of the present invention is provided. As can be seen in FIG. 20, the flute integrity tester 100 comprises an internal mechanism 102 and a hinged cover 104 with a touchscreen 78 at a front thereof. Underneath the edges of the hinged cover 94 (when it is in its closed position, as generally seen in FIG. 13) the slot 76 can be found. In this figure, the pressure plate 48 has already descended against the support plate 46 by the force sensing displacement mechanism 56 having extended its drive rod 64, e.g. to obtain a zero datum.

The cables inside the apparatus are not shown in these drawings for ease of reference, but see FIG. 11 as an example of the type of cables that might be provided.

A force sensing displacement mechanism 56 operates a cylinder for moving the rod up and down and in this embodiment this is via a moving coil actuator or voice coil system, although alternative modes of displacement are also possible such as mechanical, pneumatic, hydraulic, screw drive or belt drive and other known modes of displacement for rods.

Figure 34:
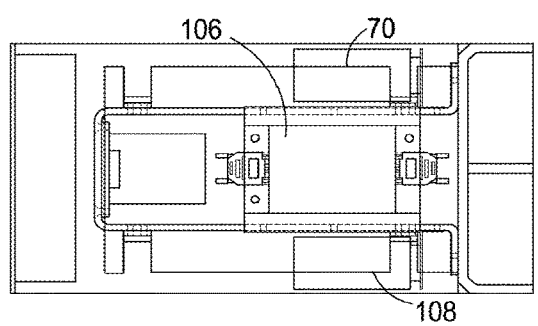

The drive mechanism is connected in this embodiment to a controller for the cylinder, that controller 106 being connected to a first power supply 70 as seen in FIG. 34.

In this embodiment, a second power supply 108 is provided on the opposite side of the frame to the first power supply 70 and it operates under a different voltage for controlling the sensor rather than the drive rod. Other voltage requirements might be needed for other controllers or sensors. A single power unit is also a possibility (or multiple voltage controllers can be provided instead).

Referring then to FIGS. 21 to 34, the steps involved in assembling the product are shown.

Figures 21, 22:
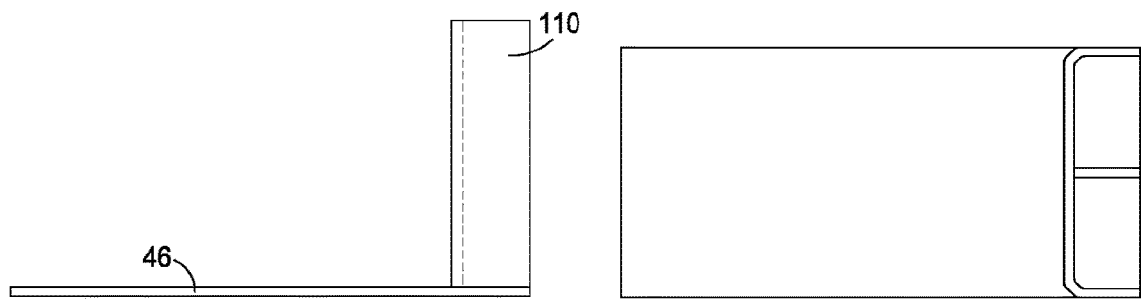
Figure 23:
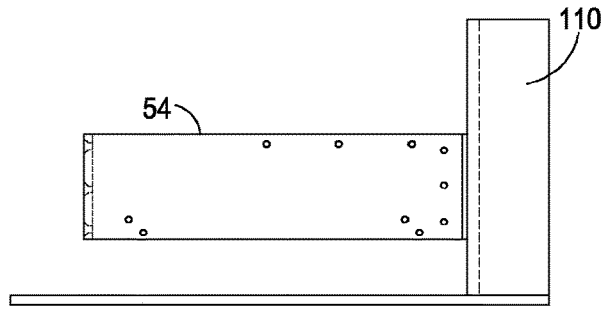

The method starts off with the base plate or support plate 46 with a back frame assembly 110 which may all be one piece, or multiple pieces attached together. FIG. 21 shows the side elevation whereas FIG. 22 shows the plan view from above. As seen it is formed of a single component, e.g. a single moulding.

Figure 24:
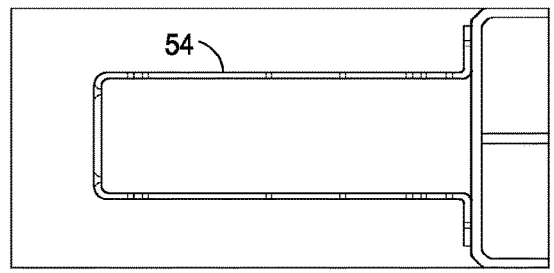
Figure 25:
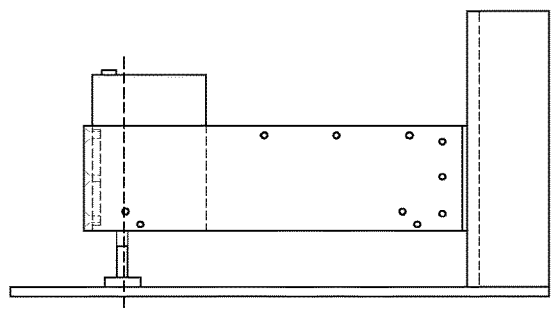
Figure 26:
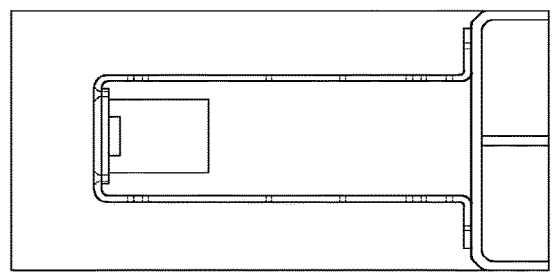
Figure 27:
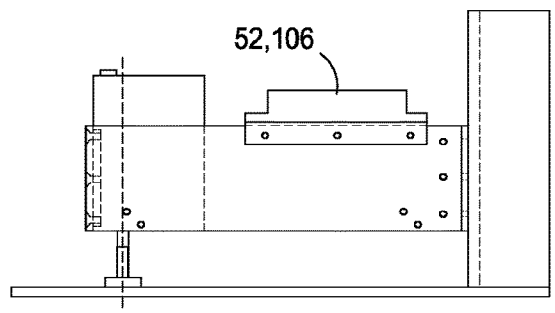
Figure 28:
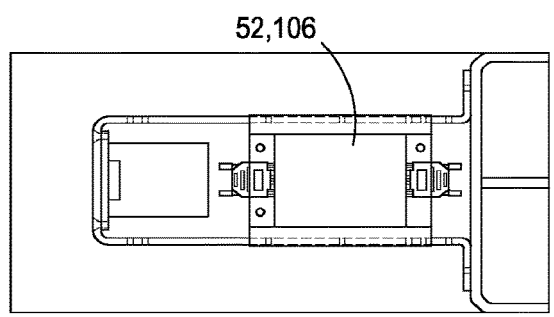
Figure 29:
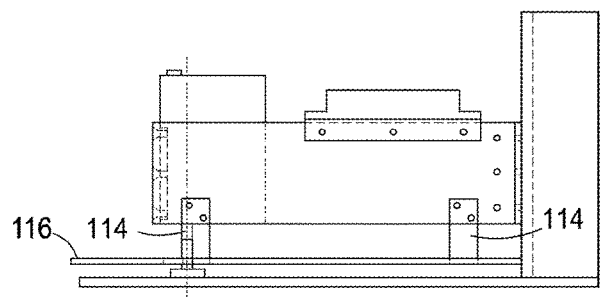
Figure 30:
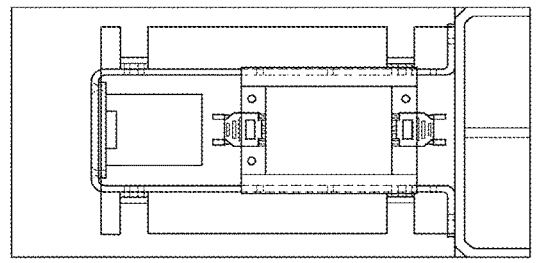

A support frame 54 is then bolted onto the back frame assembly 110 and as can be seen in FIG. 24, the frame 54 of this embodiment has a generally U shaped configuration for receiving the force sensing displacement mechanism 56, or an actuator therefor, therein.

On the top thereof, the load sensors 52 or controller 106 are mounted. See FIGS. 25 to 28.

The illustrated and discussed positions of the various components are the preferred positions for this embodiment. Other component positions and arrangements are also, of course, possible instead.

Thereafter, guard plates 114 are fitted to the front and back of the unit and then a larger finger guard 116 is attached to the bases thereof to create a barrier for preventing finger access into the testing equipment. The form of the slot is thus defined. The form of the slot might instead be formed, however, by the housing of the apparatus, or the bottom edge of the cover 104.

Figure 31:
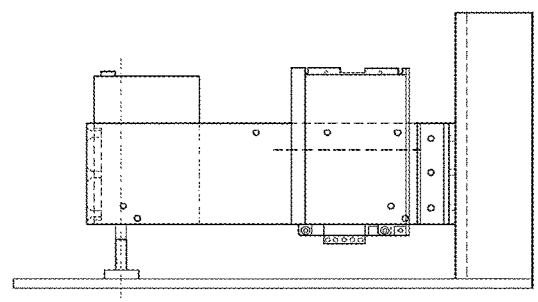
Figure 32:
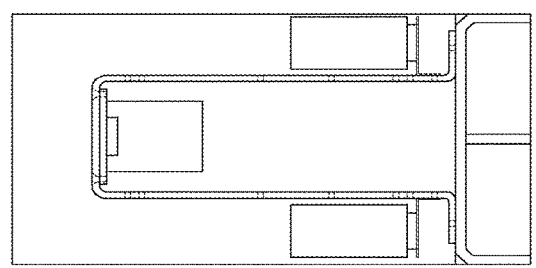
Figure 33:
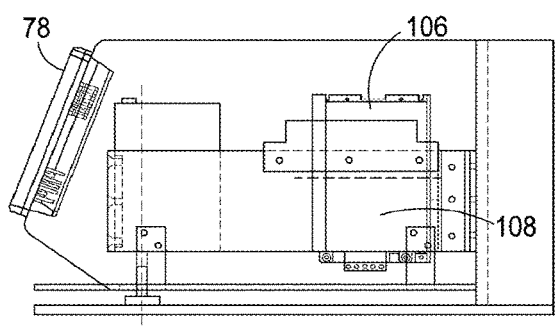

The power supply units can then be fitted, for example as shown in FIGS. 31 and 32. Herein they are attached to the sides of the frame before the cover is then attached over the top of it all.

This assembly provides a one-box testing apparatus with integrated screen and touchscreen control, and with the slot being provided therein for receiving the board directly, and without any pre-clamping thereof within the test apparatus.

The present invention therefore provides a novel testing device and a highly accurate and fast method for testing blanks and boards at the production line without creating lengthy downtimes for the production line.

Since the board types being manufactured are pre-tested to determine the standard responses to compressive loading, and the live tests only need to look at a look-up table to determine whether the actual boards in use meet the standard, the test results are quick and easy to recognise as being either a pass or a fail.

There can be times when a bespoke or untested board is specified, and thus if the board being manufactured happens not to have been pre-tested, i.e. standards are not to be found in the look-up tables, then the system can flag up the deficiency and test data can be uploaded for future use thus adding to the flexibility of the database.

Since the database of the look-up table can be constant from one production line to the next, they can be centrally controlled and networked whereby multiple machines can rely upon them, e.g. at single or multiple production line locations or in different countries. Further, when a new test result/standard is obtained and added from a lab-test, all locations can receive or access that new test result/standard.

Further, since a feed board can be tested before the final conversion, an operator does not need to rely just on a visual inspection of the feed board.

Further, the test results thereon can provide an indication as to whether a failing board met the standard prior to conversion or only after conversion. This reduces the amount of time needed to identify where the fault occurred.

In addition to the new test, calliper thicknesses are preferably also determined by the present invention since they can also be compared against standards, or used in determining the actual compression/deflection from the default state. The basic calliper value, however, allows the calliper test to be carried out and that is important since if a significant change of calliper is noted, this can also be an indication of significant damage—such as might cause the new compression test to give a false positive, whereby there is a double check.

The present invention additionally, due to the shape of the testing unit (which has a relatively wide but narrow slot, and a relatively small housing thereabove), allows the testing not only of flat blanks but also of assembled boxes—if of an adequate size, and if having accessible edges for fitting into the slot of the testing apparatus. For example, the testing apparatus preferably has a width of about 20 cm and a height above the slot of about 20 cm. Therefore a box having a top opening with a width of at least 20 cm and a length of at least 20 cm, and a hole height sufficient to allow the board to pass between the pressure plate and the support plate, will be testable along all four sides thereof.

Preferably the dimensions (height and width) are no more than 40 cm.

The present invention's illustrated test is described with reference to an average of the readings for four tested parts of a board. However, it might be preferred that a total score be used.

With the present invention, tests can be done in seconds, and generally faster than 10 seconds, whereby it is possible to recalibrate print or roller pressures in a corrugator or convertor also in seconds—rather than in minutes, since pressing a button can adjust the print or roller pressures and since the test results come back very quickly on the screen.

At present, the system is designed to be run in a separate machine to the inline corrugator and conversion devices. However, it is anticipated that it could be incorporated inline on the production line, such as through the provision of multiple test units across the widths of the corrugation or conversion machine, typically each defining a gap rather than a slot. However, the fact that someone needs to be present at the side of the machine anyway to check visual print quality and visual flute quality, having him do the test as well is not particularly going to change the product processing speed. Indeed, it may even accelerate it compared to the current procedures using the BCT or DST tests.

The present invention has therefore been described above purely by way of example. Modifications in detail may be made to the invention within the scope of the claims appended hereto.

We claim:

1. A testing machine adapted to carry out a method of non-destructively testing a structural characteristic of a corrugated board, the method comprising the steps of
    performing a non-destructive compression test on a sample region of a corrugated board of a known design,
    from said non-destructive compression test, providing a reading of said sample region's compression test characteristic,
    comparing that characteristic against a predefined acceptable characteristic that said known design of corrugated board should have, and
    concluding as to whether the board, or that region of the board, meets a required compression stiffness parameter,
wherein the testing machine comprises:
    a) a support surface on which the region of the board can lay,
    b) a pressure plate with which a testing force can be applied to an opposing side of the board so as to apply a compression force across a thickness of the board towards the support surface,
    c) at least one sensor for sensing data, the data comprising a deflection by and a force from the board, and d) a database or look-up table for checking the sensed data against a predetermined force per deflection parameter for said known design of corrugated board.

2. The testing machine of claim 1, wherein the database or look-up table comprises test data for boards of various different design types so that the apparatus can look up an appropriate predefined acceptable characteristic readings for a range of different designs of said boards.

3. The testing machine of claim 2, wherein the database or look-up table comprises data comprising at least one of a deflection response and a force response and the database or look-up table further comprises data comprising a form of a design of the board itself, the data comprising at least one of flute profile type, material weight, and material type.

4. The testing machine of claim 3, wherein the material type comprises at least one of top web material, bottom web material, flute material, ply structure, and calliper.

5. The testing machine of claim 2, wherein the database or look-up table comprises data comprising at least one of first point-failure deflections, first-point failure forces, second-point failure deflections and second-point failure forces, wherein the predefined acceptable characteristic comprises at least one of the first point failure deflections and the first-point failure forces.

6. The testing machine of claim 5, wherein the database or look-up table further comprises third-point failure deflections and third-point failure forces.

7. The testing machine of claim 1, wherein the testing machine is adapted to carry out the non-destructive compression test using a degree of compression of the board amounting to less than 1 mm.

8. A pre-formed blank having structural characteristics and being ready for assembly into a packaging or box, said pre-formed blank comprising a top ply, a bottom ply and at least one corrugate therebetween, and additionally comprising a certification with respect to the structural characteristics thereof which have been authenticated during a production run for said pre-formed blank using the testing machine of claim 1.

9. A corrugated blank manufacturing line implementing the testing machine of claim 1, the line comprising a corrugator and a converter, the line further using calibrated roller pressures for the corrugator or the converter for a particular run of blanks or products made from said blanks, the roller pressures being calibrated by feedback from the testing machine, the line using the calibrated roller pressures to adjust at least one of a roller gap, a roller alignment, and a roller pressure of the corrugator or the converter.

* * * * *